United States Patent
Bjork et al.

(10) Patent No.: US 7,125,379 B2
(45) Date of Patent: Oct. 24, 2006

(54) SURGICAL SUPPORT ARM DOCKING APPARATUS

(75) Inventors: Todd M. Bjork, River Falls, WI (US); Todd W. Sharratt, Birchwood, MN (US); Christopher Lee Berg, Crystal, MN (US); Walter J. Dobrovolny, St. Paul, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 6 days.

(21) Appl. No.: 10/698,744

(22) Filed: Oct. 31, 2003

(65) Prior Publication Data

US 2005/0065410 A1 Mar. 24, 2005

Related U.S. Application Data

(60) Provisional application No. 60/504,080, filed on Sep. 19, 2003.

(51) Int. Cl.
*A61B 1/32* (2006.01)
*B25G 3/36* (2006.01)

(52) U.S. Cl. .................. 600/213; 600/231; 600/234; 403/391

(58) Field of Classification Search ............... 600/213, 600/231, 232, 206, 210, 215, 235, 234, 324; 403/391, 385, 384, 389
See application file for complete search history.

(56) References Cited

U.S. PATENT DOCUMENTS

| 3,572,326 | A | | 3/1971 | Jensen ................... 128/20 |
|---|---|---|---|---|
| 3,749,088 | A | * | 7/1973 | Kohlmann .............. 600/215 |
| 4,434,791 | A | | 3/1984 | Darnell ................... 128/20 |
| 4,934,352 | A | | 6/1990 | Sullivan, Jr. ............ 128/20 |
| 5,375,481 | A | * | 12/1994 | Cabrera et al. ......... 74/577 M |
| 5,792,046 | A | | 8/1998 | Dobrovolny ............ 600/234 |
| 5,876,333 | A | * | 3/1999 | Bigliani et al. ......... 600/231 |
| 5,882,298 | A | | 3/1999 | Sharratt .................. 600/213 |
| 5,899,627 | A | | 5/1999 | Dobrovolny ............ 403/319 |
| 5,993,385 | A | | 11/1999 | Johnston et al. ........ 600/213 |
| 6,042,540 | A | | 3/2000 | Johnston et al. ........ 600/213 |
| 6,080,105 | A | | 6/2000 | Spears ................... 600/212 |
| 6,241,659 | B1 | * | 6/2001 | Bookwalter et al. ..... 600/231 |
| 6,530,883 | B1 | * | 3/2003 | Bookwalter et al. ..... 600/231 |
| 6,602,190 | B1 | * | 8/2003 | Dobrovolny ............ 600/234 |
| 2002/0026101 | A1 | | 2/2002 | Bookwalter et al. ..... 600/231 |
| 2003/0069479 | A1 | | 4/2003 | Phillips et al. .......... 600/228 |

FOREIGN PATENT DOCUMENTS

EP 0 089 099 A2 9/1983

\* cited by examiner

*Primary Examiner*—Pedro Philogene
(74) *Attorney, Agent, or Firm*—Westman, Champlin & Kelly, P.A.

(57) ABSTRACT

An assembly for exchanging retractor support arms within a retractor support clamp. The assembly includes a main body having a surface defining a cavity extending into the main body from a first end. A support arm having an end portion with a substantially complimentary configuration to the surface defining the cavity is positionable within the cavity. A retaining mechanism is disposed about the main body and in communication with the end portion where the retaining mechanism retains the end portion within the main body.

12 Claims, 20 Drawing Sheets

SURGICAL SUPPORT ARM DOCKING APPARATUS

CROSS-REFERENCE TO RELATED APPLICATION(S)

This application claims the benefit of U.S. Provisional Application No. 60/504,080, filed Sep. 19, 2003.

BACKGROUND OF THE INVENTION

The present invention generally relates to a surgical support apparatus for use in performing a surgical procedure. More particularly, the present invention relates to a docking system for interchanging retractor support arms having different configurations and cross sections.

A surgical support apparatus is typically disposed about a surgical site. The surgical support apparatus usually includes a field post clamped to a surgical table. The field post extends upwardly from the surgical table. A support member is clamped to the field post and extends over the surgical table.

Typically, a clamp is attached to the end of the support member. One example of such a clamp is described in U.S. Pat. Nos. 5,899,629 and 6,264,396. The clamp, in turn, engages pivot balls that are attached to two support arms. The pivot balls allow each of the support arms to be independently positioned in selected positions about the surgical site. The support arms provide the required support for mounting retractors and other surgical apparatus about the surgical site.

One drawback to the assembly of the clamp cooperating with the two support arms is that the assembly is sold as a set. To use a different configuration of support arms, another set of support arms including the clamp must typically be purchased. The cost of purchasing an additional set may be prohibitive to obtaining the differently configured support arms that would be useful when performing certain surgical procedures.

Additionally, the clamp typically comes with support arms that cooperate with that manufacturer's surgical equipment. Typically, one manufacturer's surgical equipment is not compatible with another manufacturer's surgical equipment. Oftentimes, a hospital or clinic must decide on a single supplier for its retractor support equipment. While choosing one supplier at any particular time may not be detrimental to the health care provider, over time another manufacturer may develop better equipment which is incompatible with the current manufacturer's equipment, thereby precluding the use of better equipment.

SUMMARY OF THE INVENTION

The present invention includes an assembly for exchanging retractor support arms within a retractor support clamp. The assembly includes a main body having a surface deforming a cavity extending into the main body from a first end. A support arm having an end portion with a substantially complimentary configuration to the surface defining the cavity is positionable within the cavity. A retaining mechanism is disposed about the main body and is in communication with the end portion where the retaining mechanism retains the end portion within the main body.

DETAILED DESCRIPTION OF THE PREFERRED EMBODIMENTS

Figure 1:
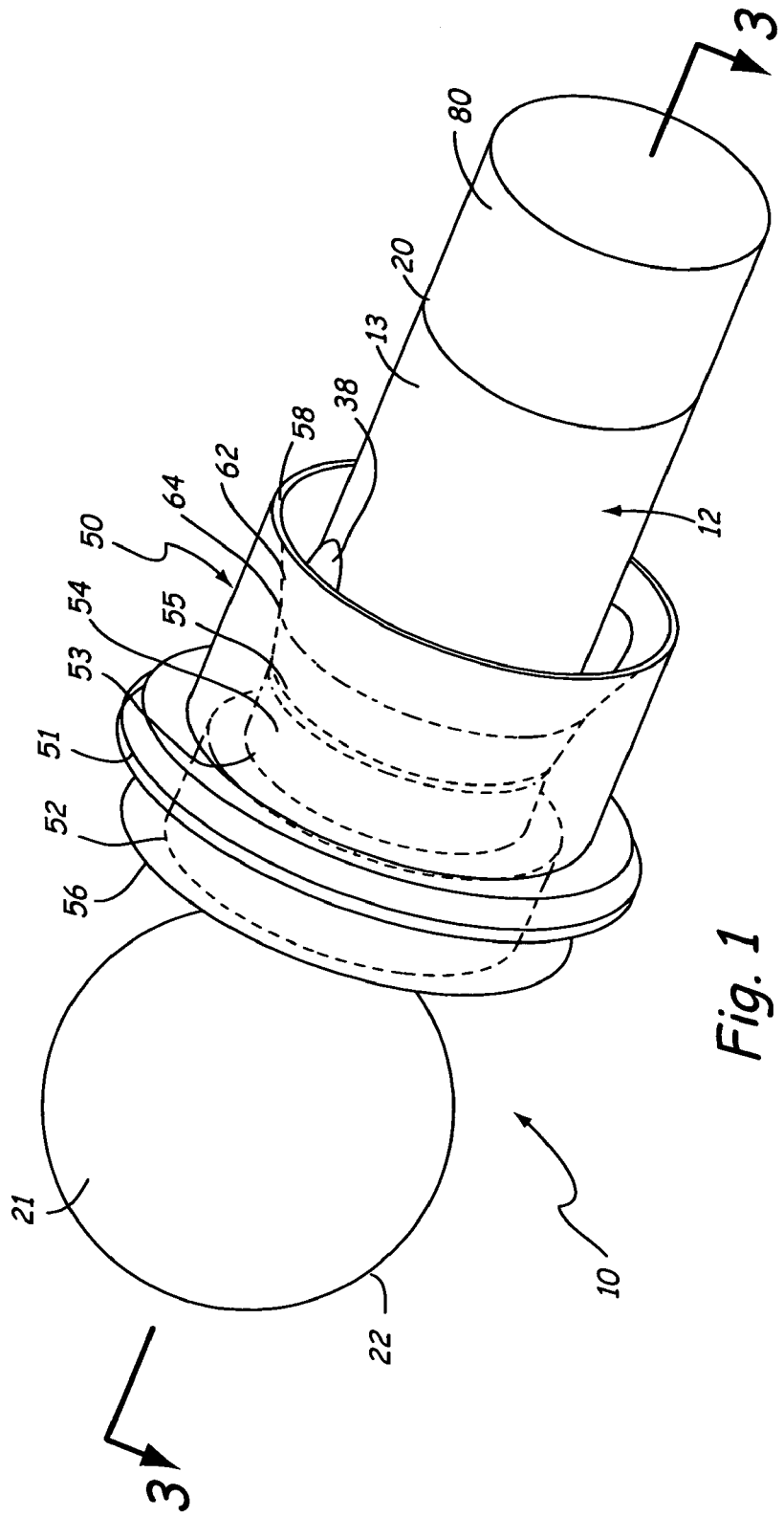
FIG. 1 is a perspective view of the docking assembly of the present invention.

The docking apparatus of the present invention is generally illustrated in FIG. 1 at 10. The docking apparatus 10 of the present invention accepts a retractor support arm 80 having various configurations and cross-sections provided that the retractor support arm 80 has a docking end 82 that is configured to dock within an internal cavity 16 of a main body 12.

Figure 4:
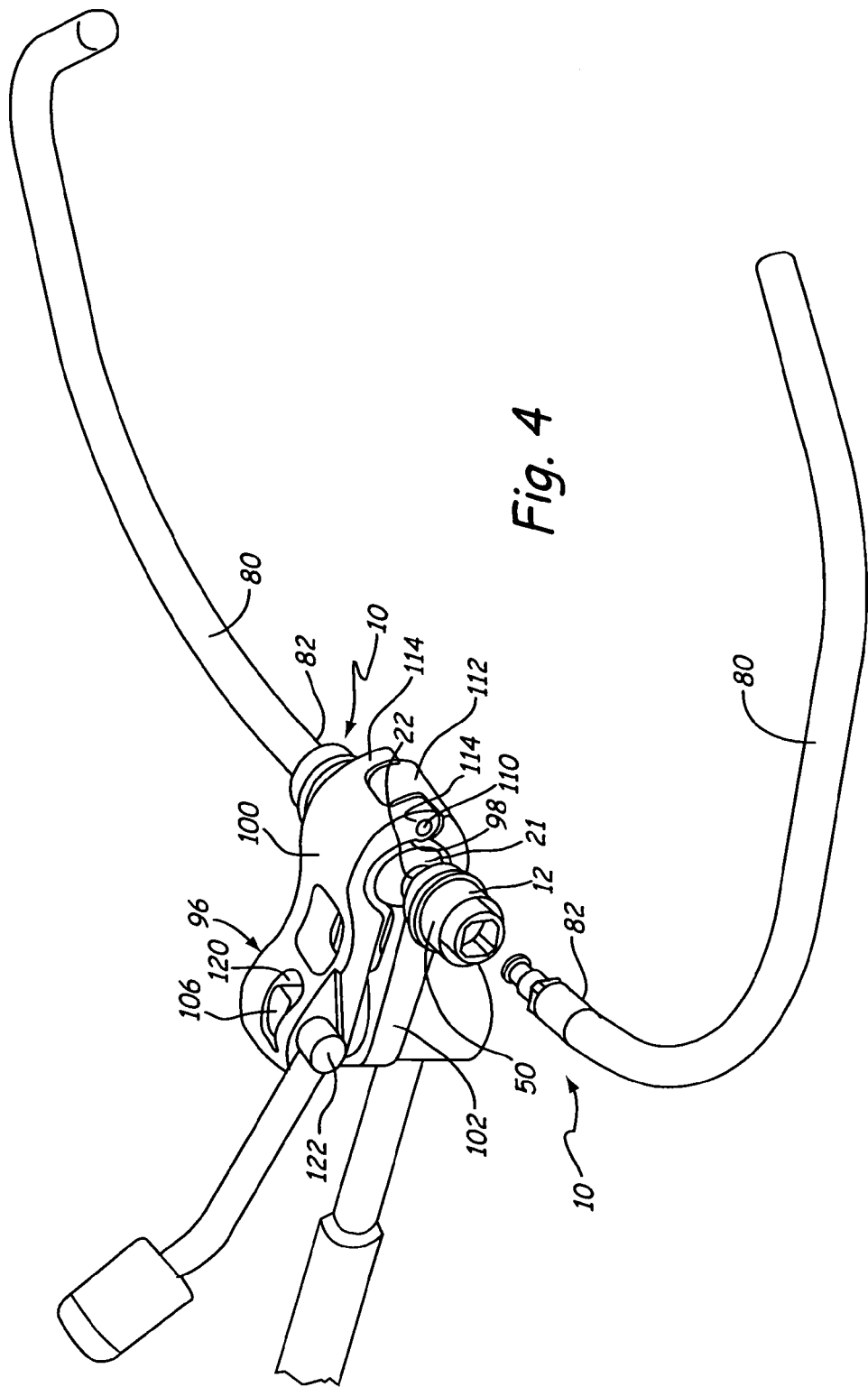
FIG. 4 is a perspective view of two docking assemblies of the present invention positioned in a clamp.

Referring to FIG. 4, a pivot ball 21 attached to a second end 22 of the main body 12 is positioned within a clamping bore 98 of a clamp 96. The pivot ball 21 is movable within the clamping bore 98 and allows the retractor support arm 80 to be positioned in a select position. With the retractor support arm 80 in the selected position, the clamp 96 is positioned into a clamping position such that the support arm 80 is retained in the selected position.

Figure 5:
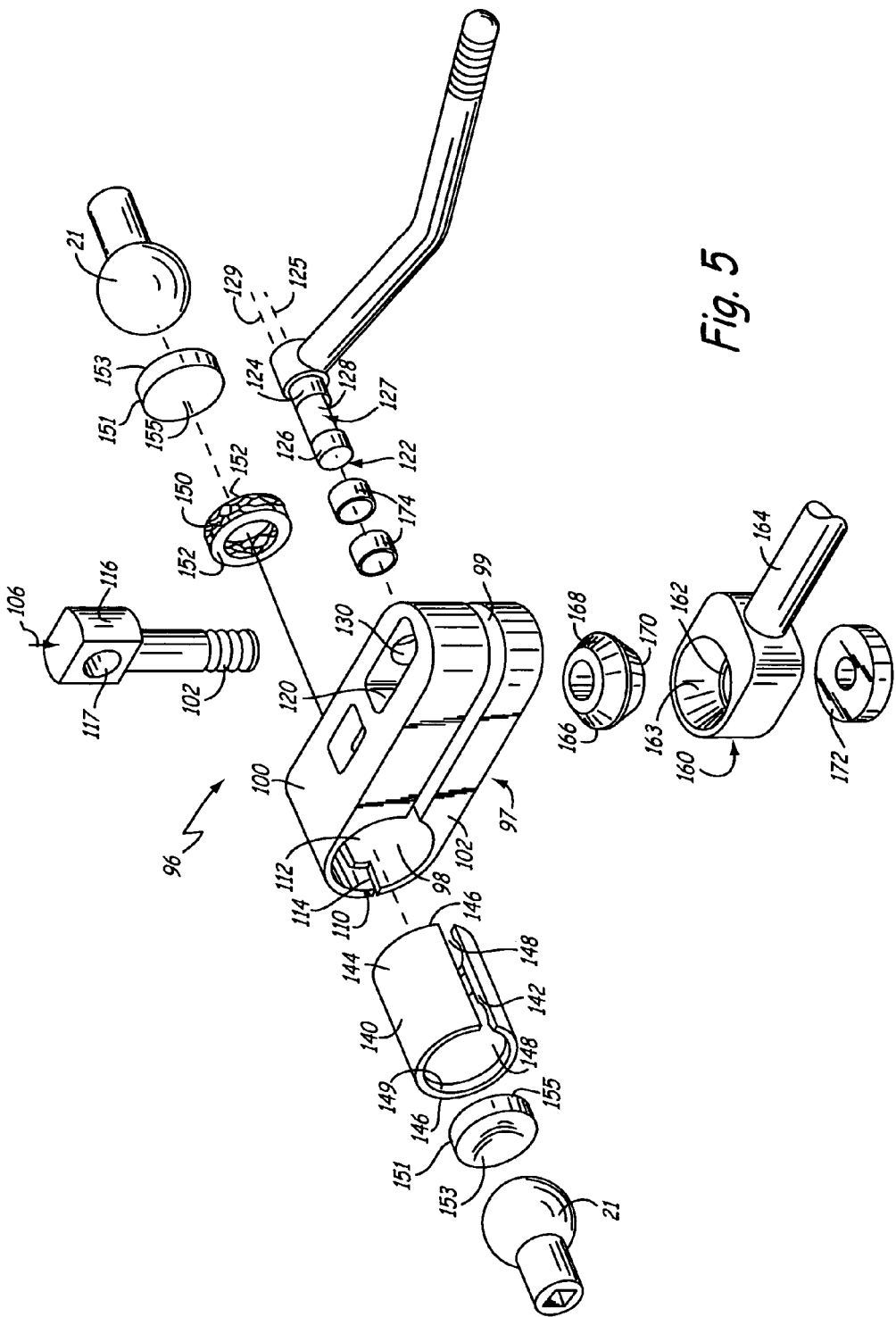
FIG. 5 is an exploded view of the clamp of the present invention.

Referring to FIGS. 4 and 5, an exemplary clamp 96 includes upper and lower resilient legs 100, 102 that define the clamping bore 98 that accepts pivot balls 21 of two separate docking apparatus 10. The upper and lower resilient legs 100, 102 separated by a slot 99 are hinged together with a pin 110 positioned within aligned through bores (not shown) of exterior extensions 114 of the upper leg 100 and an interior extension 112 of the lower leg 102. Other clamps that accept and engage pivot balls are within the scope of the invention including, but not limited to, clamps that engage a single pivot ball.

A shaft 106 is positioned within shaft passing bores 120 and (not shown), of the upper and lower legs 100, 102, respectively. A head 116 of the shaft 106 is positioned within the shaft-passing bore 120 of the upper leg 100. The shaft passing bore 120 is elongated to allow the required movement of a head 116 of the shaft 106 when the clamp 96 is positioned from the non-clamping position to the clamping position and also in the reverse direction.

A camming pin 122 is positioned within a through bore 117 in the head 116 of the shaft 106 that is aligned with through bores 130 and (not shown), in the upper leg 100 such that the camming pin 122 is rotatably secured within the upper leg 100. The camming pin 122 includes end portions 124, 126, respectively, that are positioned within the bores 130 and (not shown), respectively, and an intermediate portion 128 positioned within the through bore 117 in the head 116 of the shaft 106.

The end portions 124, 126 and the intermediate portion 128 are generally cylindrical in shape and are located adjacent one to another. The end portions 129, 126 are centered about a rotational axis 125 and are captivated within the through bores 136 and (not shown), respectively. The captivated end portions 124, 126 rotatably support the intermediate portion 128 within the through bore 117 within the head 116 of the shaft 106.

To further enhance the operation of the clamp 96, the clamp 96 preferably includes a pair of sleeve bearings 174, as most clearly illustrated in FIG. 5. The sleeve bearings 174 are placed over the end portions 124, 126 within the bores 130 and (not shown) to reduce friction between the end portions 124, 126 and the upper leg 100.

The intermediate portion 128 is eccentrically coupled between the end portions 124, 126 respectively. The intermediate portion 128 includes an outer circumferential surface 127 having an axis 129 that is spaced from the rotational axis 125 the camming pin 122 by a selected distance. The distance separating the axis 125 of the camming pin 122 and the axis 129 of the intermediate portion 128 generally determines the maximum distance that the camming pin 122 moves the shaft 106 relative to the first clamping member 97 and a second clamping member 160 attached to distal end of the shaft 106. Preferably, the distance separating the axis of the camming pin and the axis of the intermediate portion 128 is sufficient to frictionally secure the pivot balls 21 within the clamping bore 98 and secure the second clamping member 160 to the first clamping member 97.

The clamping bore 98 is adapted to receive a sleeve 140. The sleeve 140 has a slot 142 that allows the sleeve 140 to constrict in response to a force applied to an outer surface 144 of the sleeve 140 such as when the first and second legs 100, 102 are moved towards each other.

The sleeve 140 includes a semi-circular channel 148 that extends around an inner surface 149 proximate each end 146. The channels 148 are each shaped to conform with an outer surface of the pivot balls 21 to increase the surface area over which the sleeve 140 engages the pivot balls 21. The increased surface area provided by the channels 148 not only enhances the ability of the clamp 96 to secure the support arms 80 in the selected position when the clamp 96 is in the clamping position but the increased surface area contact between the sleeve 140 and the pivot balls 21 also assists to retain the support arms 80 in the selected position when the clamp 96 is in the non-clamping position.

The clamp 96 also preferably includes bushings 151 separated a spring 150 which is positioned in the sleeve 140 that have concave surfaces 153 that engage the pivot balls. The bushings 151 are preferably constructed from a strong durable plastic such as Vitrex PEEK, a linear aromatic polymer of poly(alyletherketone) and prevent wear on the pivot balls 21 and ends 152 of the spring 150. The bushings 151 have flat surfaces 155 that engage the ends 152 of the spring 150 to secure the bushings 151 proximate the spring 150. The spring 150 is selected with sufficient resiliency so that the spring 150 biases the pivot balls 21 apart from each other and into the inner surface 149 of the sleeve 140. The spring 150 thereby retains the pivot balls 21 in a selected position with respect to the sleeve 140 when the clamp 96 is in the non-clamping position. The spring 150 also permits the pivot balls 21 to be pivoted within the sleeve 140 in response to manual force placed on the support arm 80 to which the pivot ball 21 is connected.

The second clamping member 160 has a bore 162 formed therein that accepts the distal end of the shaft 106. To maintain the first clamping member 97 and the second clamping member 160 in an assembled configuration while allowing the clamp 96 to be moved between the non-clamping open and clamping positions, a nut 172 is secured to a threaded portion 105 of the shaft 106.

An extension rod 164 is preferably fixedly attached to the second clamping member 160. While fixedly attaching the extension rod 164 to the second clamping member 160 reduces the complexity of arranging the retractor support apparatus, one of ordinary skill in the art will appreciate that it is also possible to fabricate the second clamping member 160 in other configurations while remaining within the scope of the present invention.

To enhance the ability to retain the first clamping member 97 in a desired position with respect to the second clamping member 160 when the clamp 96 is in the clamping position, a bushing 166 is preferably positioned between the first clamping member 97 and the second clamping member 160. The bushing 166 preferably has a frustro-conical upper surface 168 and a frustro-conical lower surface 170.

The lower leg 102 preferably includes a frustro-conical lower surface (not shown) that substantially surrounds the shaft passing bore (not shown). The frustro-conical lower surface (not shown) is preferably orientated at substantially the same angle as the frustro-conical upper surface 168 so that the frustro-conical surfaces 168, (not shown) are substantially in contact with each other when the bushing 166 is placed adjacent to the first clamping member 97, respectively.

Similarly, the second clamping member 160 preferably includes a frustro-conical upper surface 163 that extends around a bore 161. The frustro-conical upper surface 163 is preferably oriented at substantially the same angle as the frustro-conical lower surface 170 so that the frustro-conical surface 163 and 170 are substantially in contact with each other when the bushing 177 is placed adjacent to the second clamping member 160.

The clamp 96 is positionable between a first position where the pivot balls 21 are independently rotatable within the clamping bore 98 and the first clamping member is rotatable with respect to the second clamping member 160 and a second position where the pivot balls 22 are fixedly positioned within the clamping bore 98 of the first clamping member 96 and the first clamping member 96 is fixed in a selected position with respect to the second clamping member 160. As the clamp 96 is positioned into the second clamping position, the upper and lower legs 100, 102 are forced together by the camming pin 122 that engages the shaft 106 positioned through the upper and lower legs 100, 102. The upper and lower legs 100, 102 pivot towards each other about the pin 110 such that the two pivot balls 21 are frictionally retained within the clamping bore 98. Additionally, the first clamping member 97 is frictionally secured to the second clamping member 160 by the engagement of the frusto-conical surfaces of 168, 170 of the bushing 160 with the frusto-conical surface (not shown) of the second leg 102 and the frusto-conical surface 163 of the second clamping member 160, respectively.

Figure 2:
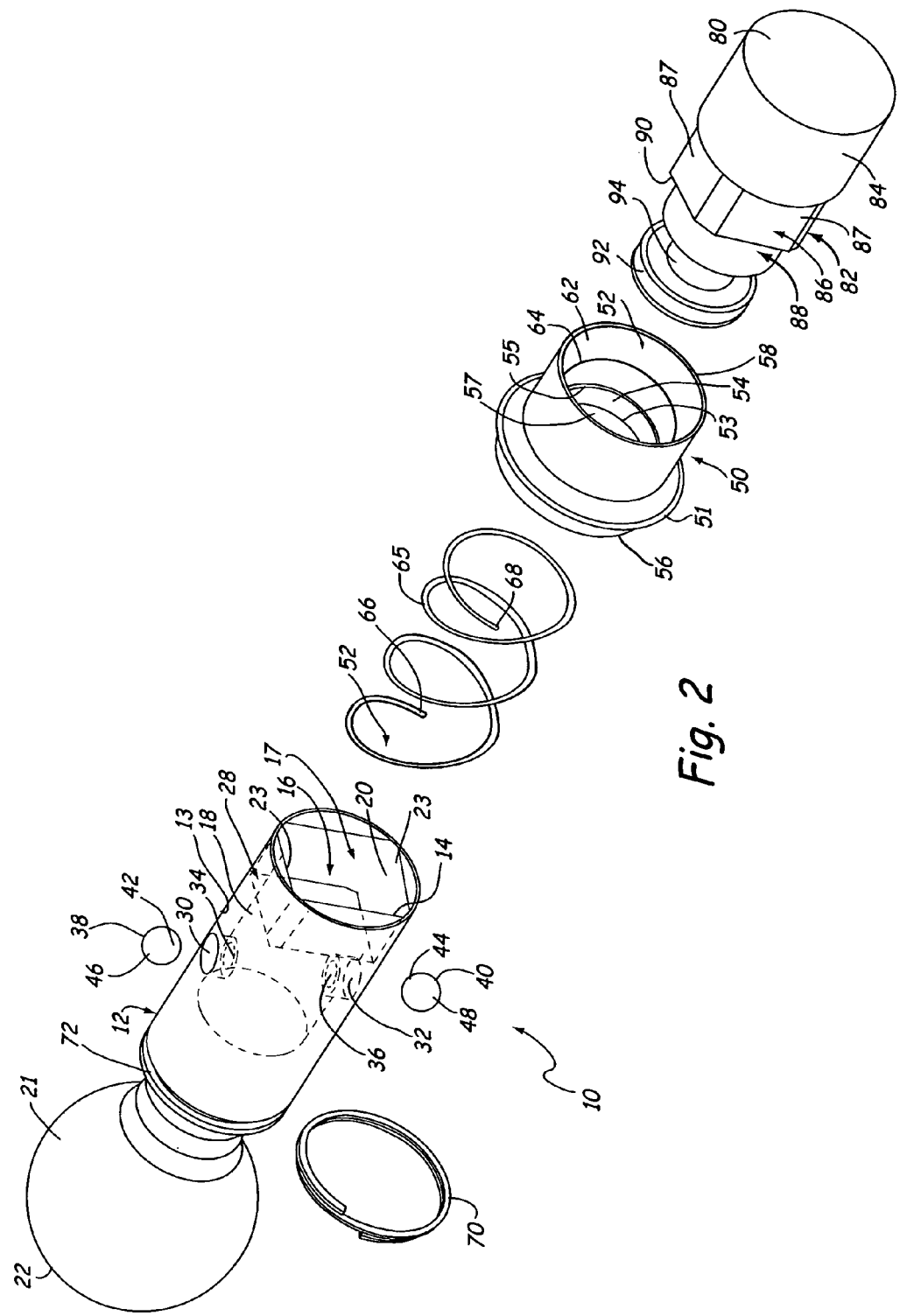
FIG. 2 is an exploded view of the docking assembly of the present invention.
Figure 3:
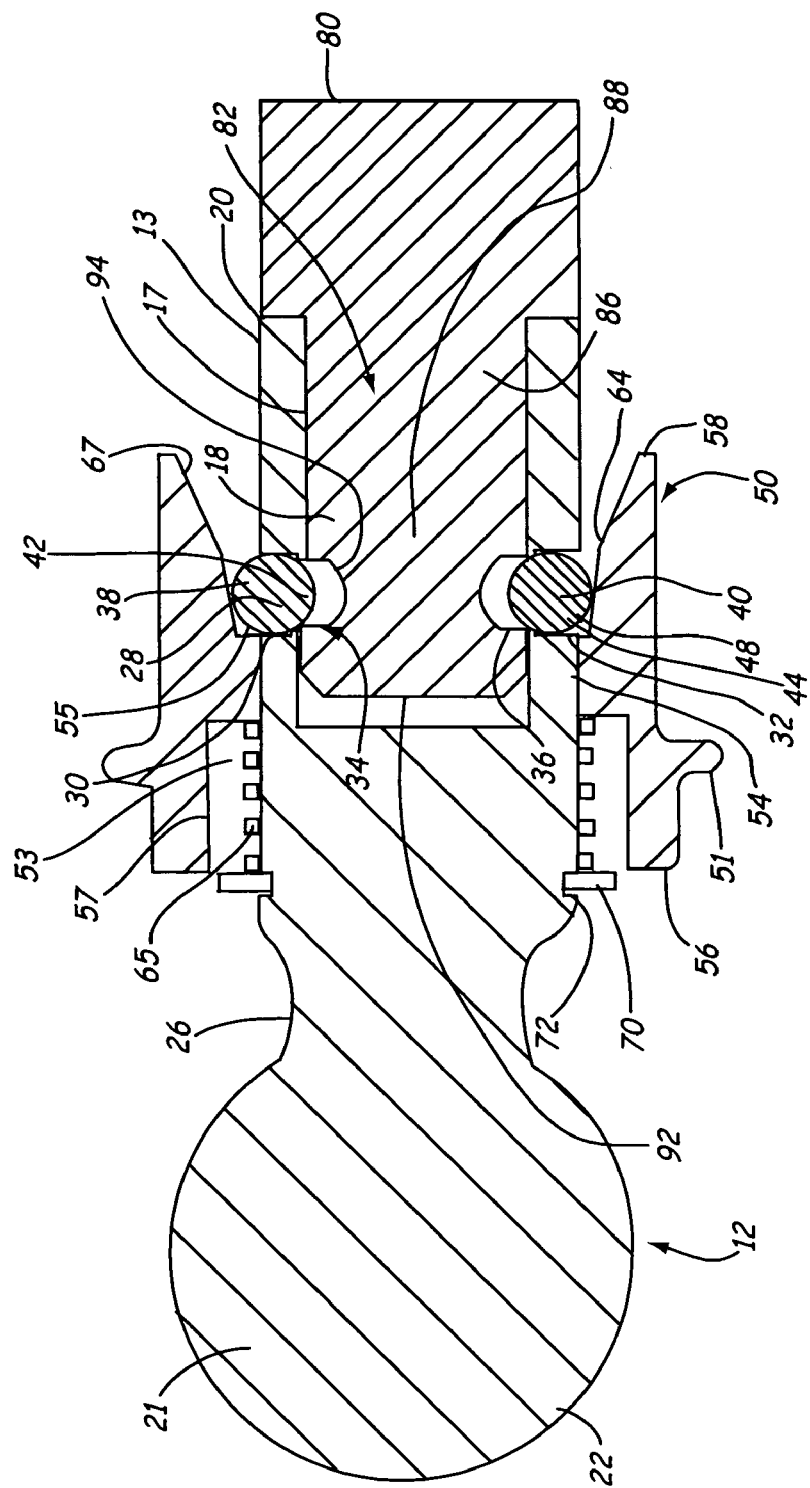
FIG. 3 is a sectional view of the docking assembly of the present invention along section line 3—3 of FIG. 1.

Referring to FIGS. 2 and 3, the docking end 82 of the retractor support arm 80 is positioned within the cavity 16 through a first end 20 and retained within the main body 12 by a retaining assembly 49 that engages the docking end 82 of the retractor support arm 80. The docking end 82 of the retractor support arm 80 is positioned within the internal cavity 16 where the docking end 82 has a substantially complementary configuration to a surface 14 defining the internal cavity 16.

With the docking end 82 positioned within the internal cavity 16, a first portion 86 of the docking end 82 having a generally polygonal cross-section engages a first portion 17 of the surface 14 defining the internal cavity 16 having a substantially complimentary generally polygonal cross-section. Flat surfaces 87 of the first portion 86 of the docking end 82 engage flat surfaces 23 of the first portion 17. The engagement of the flat surfaces 87, 23 prevents the support arm 80 from rotating with respect to the main body 12. The first portions 17, 82 preferably have generally square cross-sections with rounded corners, although other generally polygonal cross-sectional configurations are within the scope of the invention.

With the first portion 86 of the docking end 82 positioned within the first portion 17 of the surface 14 defining the internal cavity 16, a second portion 88 extending from the first portion 86 is positioned within a second portion 18 of the surface 14 defining the internal cavity 16. Both second portions 86, 18 are generally circular in cross section, although other cross-sectional configurations are within the scope of the invention.

A depth of the docking end 82 within the internal cavity 16 is limited by a shoulder 90 located at a junction of the first and second portions 86, 88, respectively, abutting a shoulder 28 of the surface 14 defining the internal cavity 16 at a junction of the first and second portions 17, 18, respectively. With the shoulder 90 abutting the shoulder 28, the retaining assembly 49 engages and retains the docking end 82 within the main body 12.

The retaining assembly 49 preferably includes spherical members 38, 40 disposed within through bores 30, 32 intersecting the second portion 18 of the surface 14 defining the internal cavity 16 where the spherical members 38, 40 engage an actuating mechanism 50. Other retaining assemblies are also within the scope of the invention.

First portions 42, 44 of the spherical members 38, 40, respectively, are positioned into the internal cavity 16 and engage an annular groove 94 within the second portion 88. The first portions 42, 44 are defined as the portions of the spherical members 38, 40, respectively, that extend into the internal cavity 16.

The members 38, 40 are preferably spherical in configuration which allows the members 38, 40 to rotate within the through bores 30, 32, respectively. Although, the preferred configuration is a sphere, other spheroidal configurations for the members 38, 40 are within the scope of the invention. What is meant by spheroidal is objects having portions of the outer surface which are arcuate although the portion of the outer surface need not be defined by a consistent radial distance from a center of the member such as ellipsoids.

In an exemplary embodiment, the main member 12 has two through bores 30, 32 opposite each other. However, the main member 12 may have only one through bore or more than two through bores while practicing the present invention.

Constricted openings 34, 36, of the through bores 30, 32, respectively, retain the spherical members 38, 40, within the through bores 30, 32, respectively. The constricted openings 34, 36 prevent the spherical members 38, 40 from falling out of the through bores 30, 32, respectively, and into the internal cavity 16 when the end 82 is removed from the internal cavity 16.

Referring to FIGS. 1–3, the actuating mechanism 50 is positioned about an exterior surface 13 of the main body 12 and is in a first position when an internal frusto-conical surface 62 contacts and exerts a force upon second portions 46, 48 of the spherical members 38, 40, respectively. The second portions 46, 48 are defined as the portions of the spherical members 30, 32, respectively, that extend above the exterior surface 13.

The force exerted upon the second portions 46, 48 of the spherical members 38, 40 forcibly position the first portions 42, 44, respectively, within the annular groove 94. With the first portions 42, 44 forcibly positioned within the annular groove 94, the docking end 82 of the retractor support arm 80 is retained within the main body 12.

The actuating mechanism 50 is biased into the first position by a compression spring 65 that is positioned about the external surface 13 of the main body 12. A first end 66 of the compression spring 65 contacts a snap ring 70 positioned within an annular groove 72 on the main body 12. A second end 68 of the compression spring 65 contacts a first surface 53 of a shoulder 54 that extends into a through bore 52 and is positioned between a first end 56 and a second end 58 of the actuating mechanism 50.

The actuating mechanism 50 is retained in the first position by the second portions 46, 48 of the spherical members 38, 40, respectively. The second portions 46, 48 engage a second surface 55 of the shoulder 54 which prevents further movement of the actuating mechanism 50 along the main member 12 in the direction of the bias of the compression spring 65.

The actuating mechanism 50 is positioned into the second position by applying manual force that overcomes the bias of the compression spring 65. The actuating mechanism 50 is positioned into the second position when the second end 58 is proximate the second portions 46, 48 of the spherical members 38, 40, respectively. The actuating mechanism 50 includes a raised surface 51 about a circumference of the actuating mechanism 50 which provides a gripping surface for positioning the actuating mechanism 50 into the second position.

With the actuating mechanism 50 in the second position, the internal frusto-conical surface 62, which is a portion of the through bore 52, is disengaged from the second portions 46, 48. The pitch of the internal frusto-conical surface 62 increases at about a midpoint 64 between the second surface 55 of the shoulder 54 and the second end 58 to provide the necessary clearance for the actuating mechanism 50 proximate the second end 58 to disengage the internal frusto-conical surface 62 from the second portions 46, 48 of the spherical members 38, 40, respectively.

With the actuating mechanism 50 in the second position, manual force is applied to the retractor support arm 80 substantially in an axial direction to the docking end 82. A distal end portion 92 of the docking end 82 contacts the first portions 42, 44 of the spherical members 38, 40, respectively, and displaces the first portions 42, 44 from the internal cavity 16. With the first portions 42, 44 of the spherical members 38, 40, respectively, displaced from the internal cavity 16, the docking end 82 can be removed from the main body 12 with additional manual force.

To provide the necessary travel for the actuating mechanism 50 to move between the first position and the second position, the through bore 52 proximate the first end 56 accommodates the snap ring 70. A diameter of the through bore 52 is larger than an external diameter of the snap ring 70 such that the actuating mechanism 50 proximate the first end 56 passes over the snap ring 70 as the actuating mechanism 50 is moved from the first position to the second position.

In operation, a retractor support arm 80 is positioned within the docking apparatus 10 by positioning the docking end 82 within the internal cavity 16 until the distal end portion 92 contacts the first portions 42, 44 of the spherical members 38, 40, respectively. The actuating mechanism 50 is positioned into the second position with manual force such that the internal frusto-conical surface 62 is disengaged from the second portions 46, 48 of the spherical members 38, 40, respectively.

Additional manual force is applied to the support arm 80 in a substantially axial direction to the docking end 82 such that the distal end portion 92 displaces the first portions 42, 44 from the internal cavity 16. With the first portions 42, 44 displaced from the internal cavity 16, the docking end 82 is further positioned within the internal cavity 16 until the shoulder 90 of the docking end 82 abuts the shoulder 28 of the surface 14 defining the internal cavity 16.

With the shoulders 90, 28 abutting, the flat surfaces 87 of the first portions 86 of the end 82 engage the flat surfaces 23 of the first portion 17 of the surface 14 defining the internal cavity 16. The flat surfaces 87, 23 engage to prevent rotation of the docking end 82 within the main body 12, respectively. Additionally, the annular groove 94 is aligned with the through bores 30, 32 when the shoulder 90 abuts the shoulder 28.

With the docking end 82 positioned within the internal cavity 16, the manual force is removed from the actuating mechanism 50 such that the compression spring 65 forces the actuating mechanism 50 into the first position. With the actuating mechanism 50 in the first position, the internal frusto-conical surface 62 contacts the second portions 46, 48 of the spherical members 38, 40, respectively, and forces the first portions 42, 44 of the spherical members 38, 40, respectively, into the annular groove 94. With the first portions 42, 44 of the spherical members 30, 32, respectively, forcibly positioned within the annular groove 94, the docking end 82 is retained within the main body 12.

To remove the retractor support arm 80 from the main body 12, manual force is applied to the actuating mechanism 50 to position the actuating mechanism 50 into the second position. With the actuating mechanism 50 in the second position, the second end 58 of the actuating mechanism 50 is proximate the second portions 46, 48 of the spherical members 38, 40 such that the internal frusto-conical surface 62 is disengaged from the second portions 46, 48.

Manual force is applied to the retractor support arm 80 in a substantially axially direction to the docking end 82 such that the distal end portion 92 forces the first portions 42, 44 of the spherical members 38, 40, respectively, from the internal cavity 16. With the first portions 42, 44 of the spherical members 38, 40, respectively, displaced from the internal cavity 16, the docking end 82 of the support arm 80 is removed from the main body 12 with additional manual force.

To replace the retractor support arm 80 with another retractor support arm 80 of a different configuration but having a similarly configured docking end 82, the docking end 82 is disposed within the internal cavity 16. The actuating mechanism 50 is positioned into the second position with manual force such that the docking end 82 can be inserted into the internal cavity 16 such that the distal end portion 92 displaces the first portions 42, 44 from the internal cavity 16.

With the first portions 42, 44 displaced from the internal cavity 16, the docking end 82 is further positioned within the internal cavity 16 until the shoulder 90 abuts the shoulder 28 which aligns the annular groove 94 with the through bores 30, 32. The side surfaces 87 of the first portion 82 of the end 80 engage the side surfaces 23 of the surface 14 defining the first portion 17 of the cavity 16 to prevent rotation of the docking end 82 with respect to the main body 12.

With the docking end 82 non-rotatably positioned within the internal cavity 16, the actuating mechanism 50 is positioned into the first position by removing the manual force from the actuating mechanism 50 such that the compression spring 65 forces the actuating mechanism 50 into the first position. With the actuating mechanism 50 in the first position, the first portions 42, 44 of the spherical members 38, 40, respectively, are forcibly positioned and retained within the annular groove 94 by the engagement of the internal frusto-conical surface 62 with second portions 46, 48. With the first portions 42, 44 of the spherical members 38, 40, respectively, forcibly positioned within the annular groove 94, the docking end 82 is securely retained within the main body 12.

One skilled in the art will recognize that support arms 80 of different configurations and cross-sections are interchangeable provided the docking ends 82 of the support arms 80 are compatible with the docking apparatus 10 of the present invention. Additionally, the docking apparatus 10 of the present invention allows the health care provider to reuse the same clamping device for numerous procedures while using differently configured support arms 80.

Figure 6:
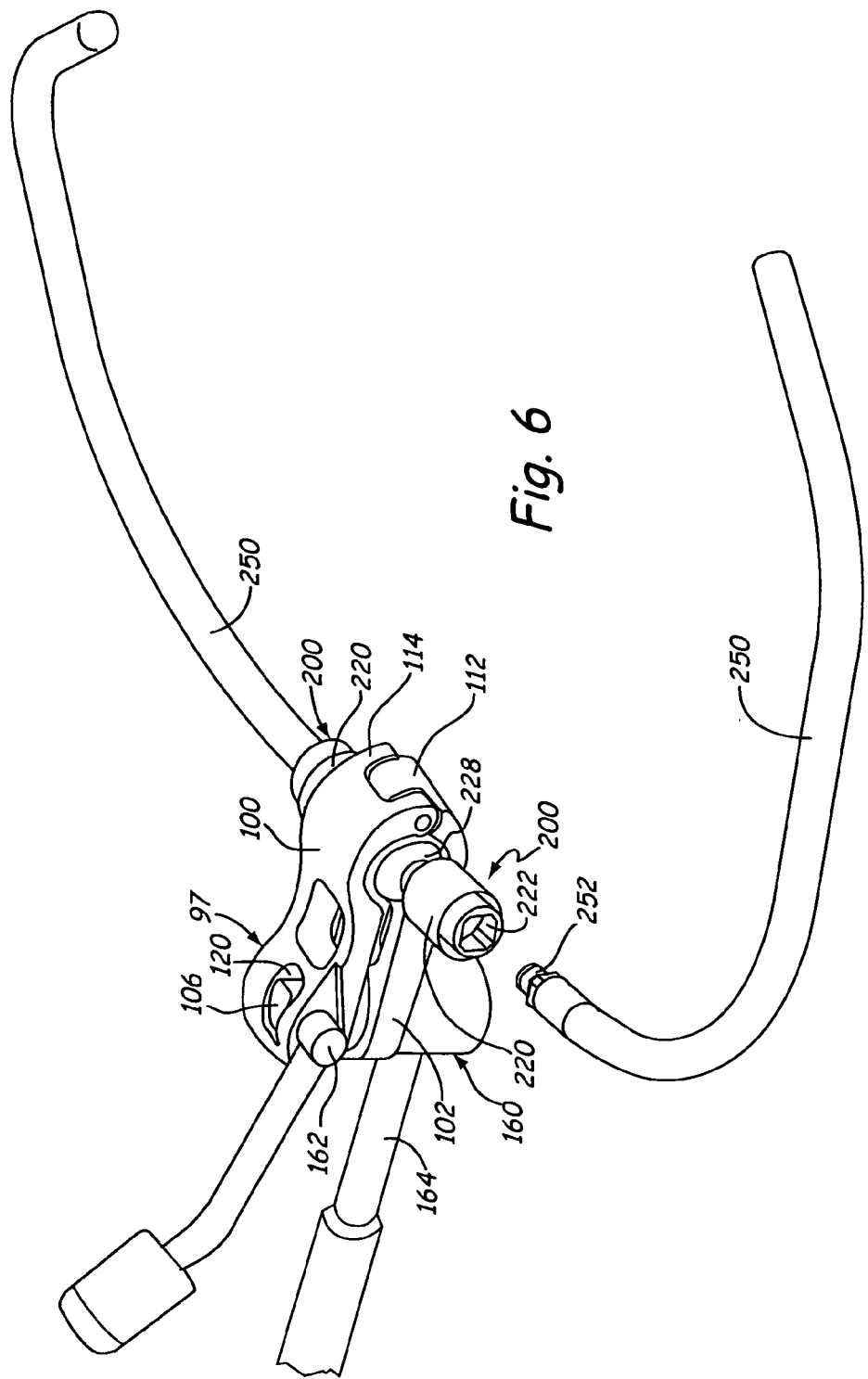
FIG. 6 is a perspective view of an alternative embodiment of the docking assembly cooperating with a clamp of the present invention.
Figure 7:
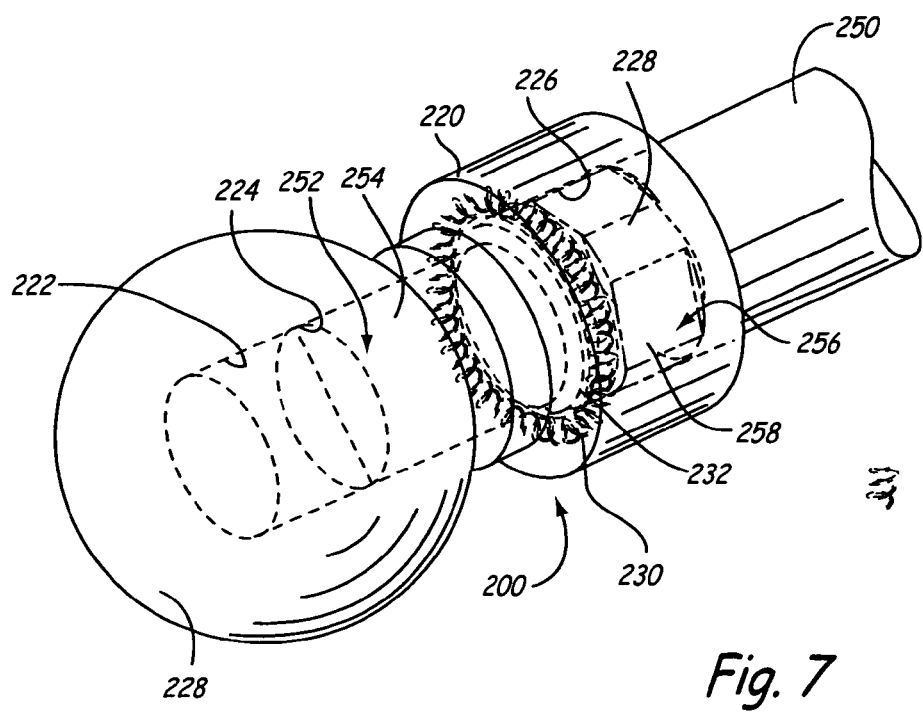
FIG. 7 is a perspective view of the alternative embodiment of the docking assembly of the present invention.
Figure 8:
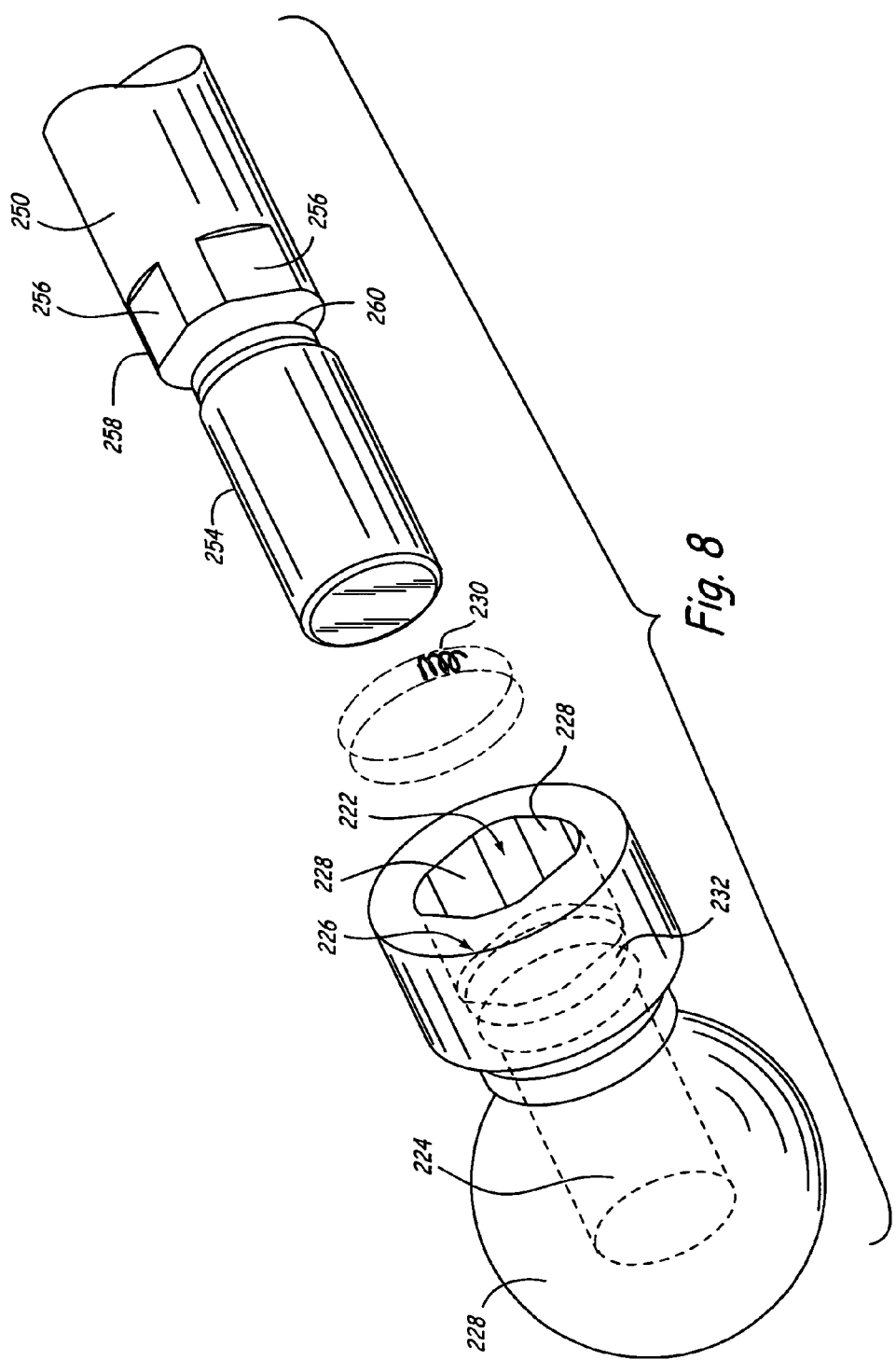
FIG. 8 is an exploded view of the alternative embodiment of the docking assembly of the present invention.

An alternative embodiment a docking apparatus of the present invention is generally depicted at 200 in FIGS. 6–8. The docking apparatus 200 of the present invention accepts a retractor support arm 250 having various configurations and cross-sections provided that the retractor support arm 250 has a docking end 252 that is configured to dock within an internal cavity 222 of a main body 220.

A pivot ball 228 attached to the main body 220 is positioned within the clamping bore 98 of the first clamping member 97 of the clamp 96. The embodiment 200 and each of the following embodiments is designed to cooperate with the clamp 96 or any other clamp that accepts one or more pivot balls.

The pivot ball 228 is movable within the clamping bore 98 and allows the retractor support arm 250 to be positioned in a selected position. With the retractor support arm 250 in the selected position, the clamp 96 is positioned into a clamping position such that the support arm 250 is secured in the selected position.

With the pivot balls 21 secured within the first clamping member 97, an end 252 of a retractor support arm 250 is positioned within an internal cavity 222 of the main body 220. As the end 252 is positioned within the internal cavity, a generally circular cross-sectional distal portion 254 is positioned within a generally circular cross-sectional portion 224 of the internal cavity 222.

The end 252 is non-rotatably fixed within the internal cavity 222 by positioning a generally square cross-sectional proximal portion 256 of the end 252 within a generally square cross-sectional proximal portion 226 of the internal cavity 222. Flat surfaces 258 of the proximal portion 256 engage flat surfaces 228 of a surface 221 defining the internal cavity 222 to prevent the end 252 from rotating within the internal cavity 222. However, generally polygonal cross-sectional proximal portions 226, 256 having three or more sides is within the scope of the invention.

With the end 252 positioned within the internal cavity 222, a coiled flexible spring 230 is positioned within an annular groove 232 on the surface 221 defining the internal cavity 222 and within an annular groove 260 on the end 252. With the coiled flexible spring 230 positioned within the annular groove 260 of the docking end 252, the support arm 250 is retained within the main body 220. The coiled flexible spring 230 is retained within the annular groove 232 of the main body 220 with a compression fit.

Manual force is axially applied to the end 252 to remove the end 252 from the internal cavity 222. Manual force causes the coiled flexible spring 230 to compress within the annular groove 232 of the main body 220 as the distal portion 254 is removed from the internal cavity 222. With the end 252 removed from the internal cavity 222, the coiled flexible spring 230 expands back into the internal cavity 222 and is capable of engaging the annular groove 260 of another end portion 252 of a support arm 250.

Figure 9:
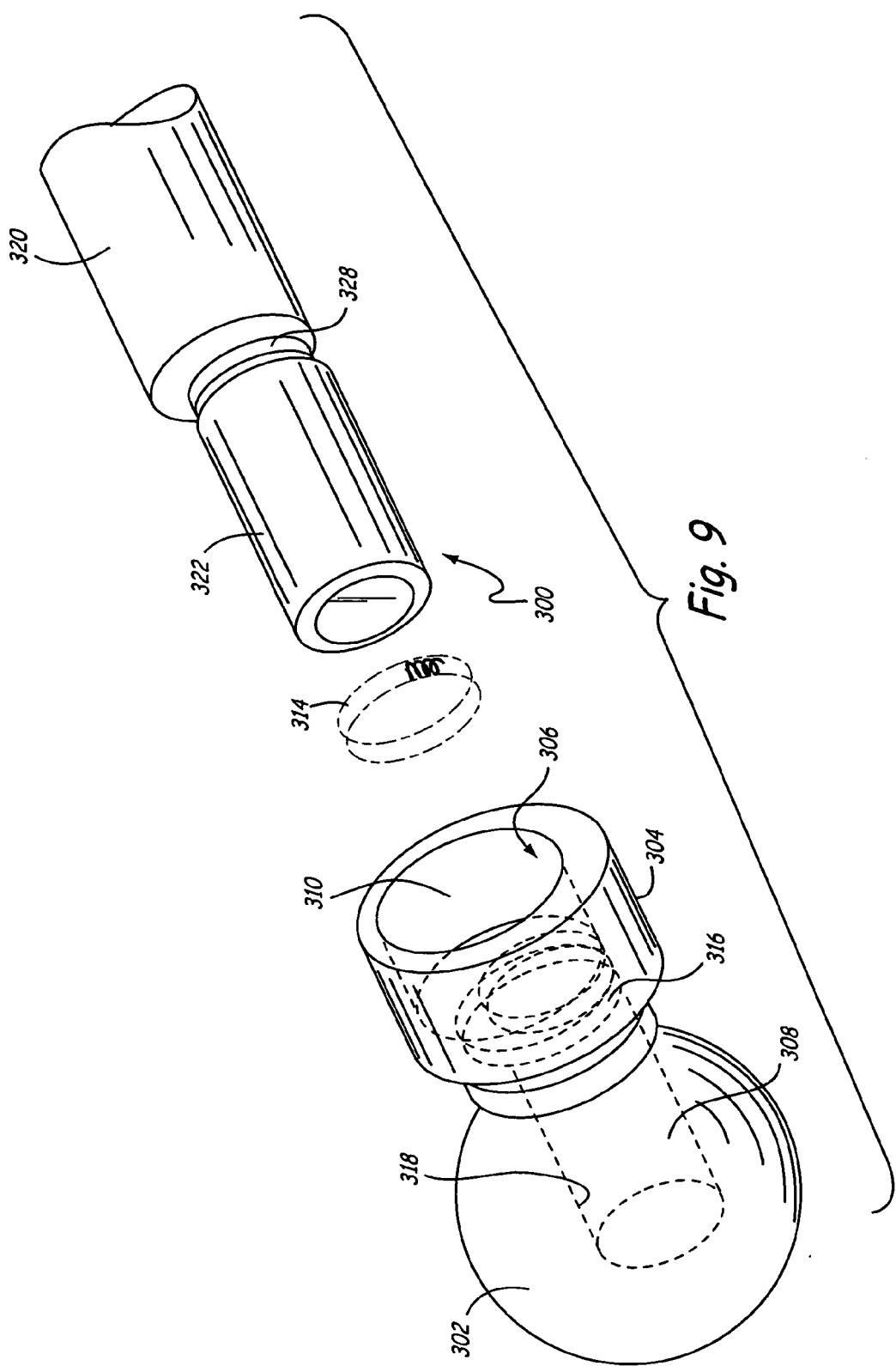
FIG. 9 is an exploded view an additional alternative embodiment of the docking assembly of the present invention.
Figure 10:
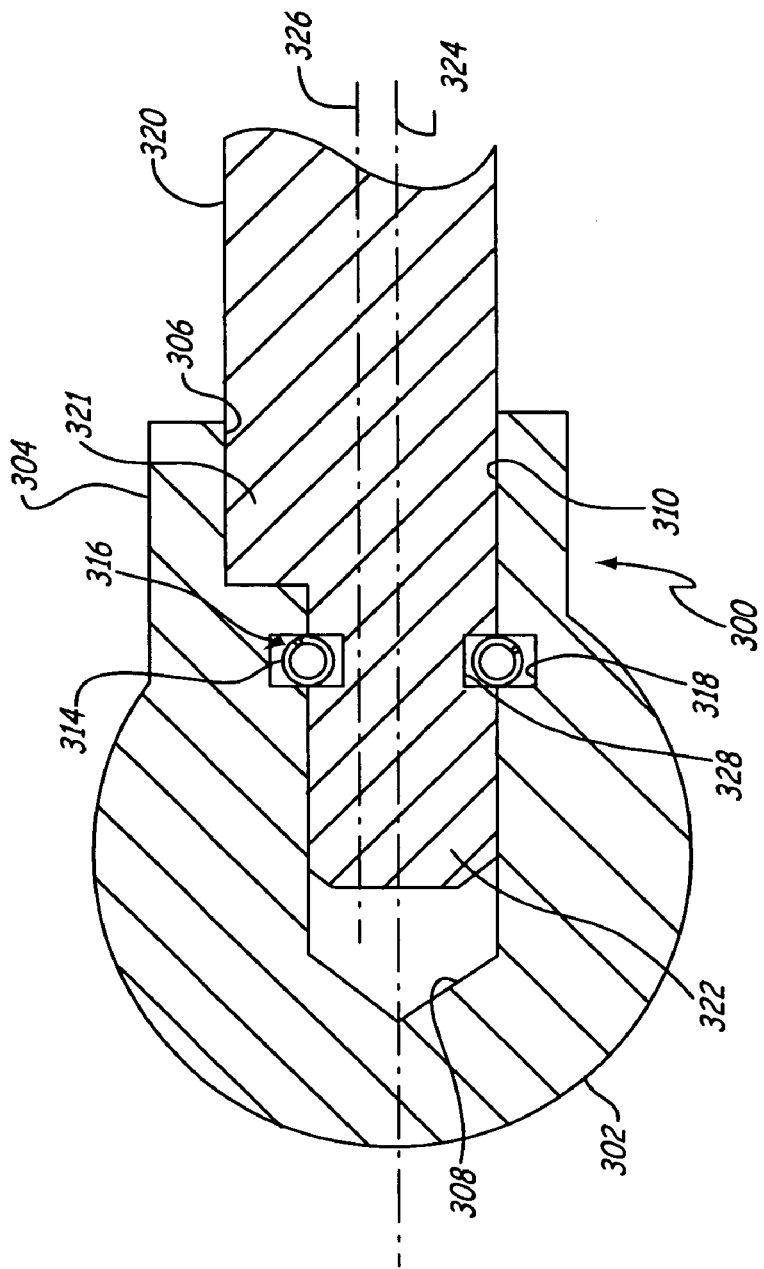
FIG. 10 is a sectional view of the alternative embodiment of the docking assembly of the present invention as illustrated in FIG. 9.
Figure 11:
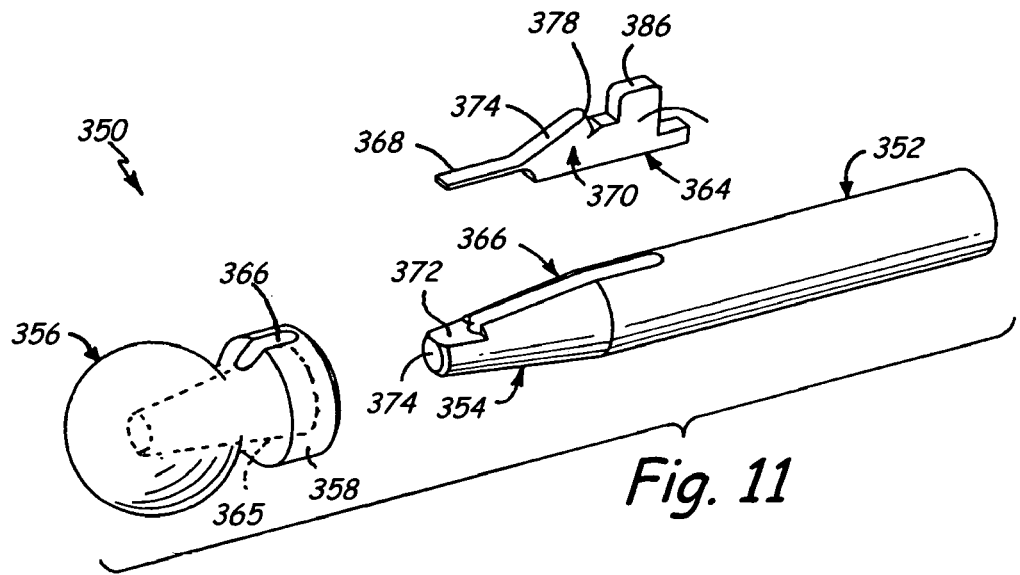
FIG. 11 is an exploded view of another alternative embodiment of the docking assembly of the present invention.
Figure 12:
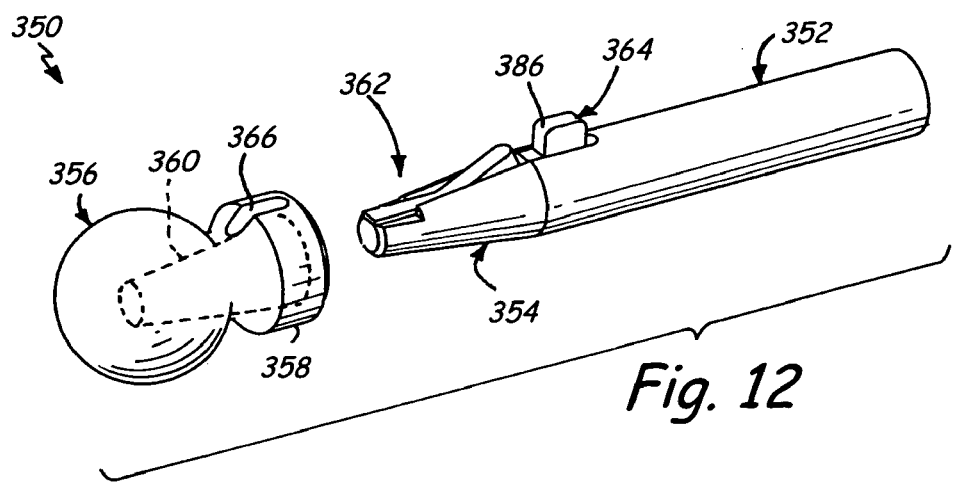
FIG. 12 is another exploded view of the alternative embodiment of the docking assembly of the present invention.

An alternative embodiment a docking apparatus of the present invention is generally depicted at 300 in FIGS. 9–10. The docking apparatus 300 of the present invention accepts a retractor support arm 320 having various configurations and cross-sections provided that the retractor support arm 320 has a docking end 322 that is configured to dock within an internal cavity 306 of a cylindrical extension 304.

The docking apparatus 300 includes a pivot ball 302 that is positioned within the clamping bore 98 of the first clamping member 97 of the clamp 96 previously described herein. The pivot ball 302 is rotatable within the clamping bore 98 and includes the cylindrical extension 304 having the internal cavity 306 that accepts the end 332 of the support arm 320.

The docking end 322, having an axis 324 offset from an axis 326 of the support arm 320, is positioned within a distal portion 308 of the internal cavity 304. Preferably, the end portion 322 and the distal portion 308 of the internal cavity 306 have generally circular cross-sectional configurations although other cross-sectional configurations of the end portion 322 and the distal portion 308 are within the scope of the invention.

Referring to FIG. 10, a portion 321 of the support arm 320 is positioned within a proximal portion 310 of the internal cavity 306. With the docking end 322 and the portion 321 of the support arm 320 positioned within the internal cavity 306, the offset axes 324, 326 prevent the support arm 320 from rotating within the internal cavity 306 of the cylindrical extension 304.

With the end portion 322 positioned within the internal cavity 306, a coiled flexible spring 314 is positioned within an annular groove 316 on a surface 318 deforminig the cavity 306 and within an annular groove 328 on the docking end 322. With the coiled flexible spring 314 positioned within the annular groove 328, the support arm 320 is retained within the cylindrical extension 304. The coiled flexible spring 314 is retained within the annular groove 316 on the cylindrical extension 304 with a compression fit.

Manual force is axially applied to the support arm 320 to remove the end 322 from the internal cavity 306. Manual force causes the coiled flexible spring 314 to compress within the annular groove 316 on the cylindrical extension 304 as the end portion 322 is removed from the internal cavity 306. With the end portion 322 removed from the internal cavity 306, the coiled flexible spring 314 expands back into the internal cavity 306 and is capable of engaging the annular groove 328 of another end portion 322 of a support arm 320.

Referring to FIGS. 11–14, an alternative embodiment is generally depicted at 350. The embodiment 350 includes a support arm 352 having an end portion 354 positioned within a cavity 360 of a main body 358 having a pivot ball 356 attached thereto.

Preferably the end portion 354 has a frusto-conical configuration. However, other configurations of the end portion 354 are within the scope of the present invention, including but not limited to, a cylindrical configuration, a cylindrical configuration having a lesser diameter than the support arm 352 and conical configuration. Whatever the configuration, the cavity 360 is configured to receive the end portion 354 of the support arm 352.

Upon cooperably mating the main body 358 and the end portion 354, a locking mechanism 362 secures the support arm 352 to the main body 358 preventing both rotational and translational movement of the support arm 354 relative to the main body 358. The locking mechanism 362 includes a locking member 364 disposed within a channeled groove 366 extending longitudinally into the end portion 354. A depth of the channeled groove 366, however, is slightly larger than a height of the locking member 364 which permits the locking member 364 to be positionable within the channeled groove 366.

Figure 13:
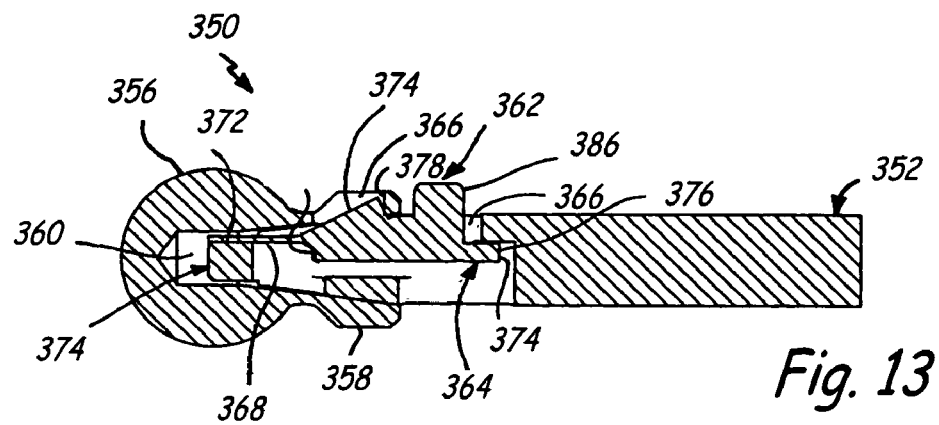
FIG. 13 is a sectional view of the alternative embodiment of the present invention of FIGS. 11 and 12.

A leaf spring 368 protrudes from a forward portion 370 of the locking member 364 and rests upon a flat surface 372 of a forward region 374 of the distal portion 354. Engaging and connecting the leaf spring 368 to the flat surface 372 urges the locking member 364 out of the channeled groove 366. However, as illustrated in FIG. 13, a rearward ledge 374 of the locking member 364 engages an upper inner surface 376 formed within the channeled groove 366, preventing further movement of the locking member 364 from the bias of the leaf spring 368.

Figure 14:
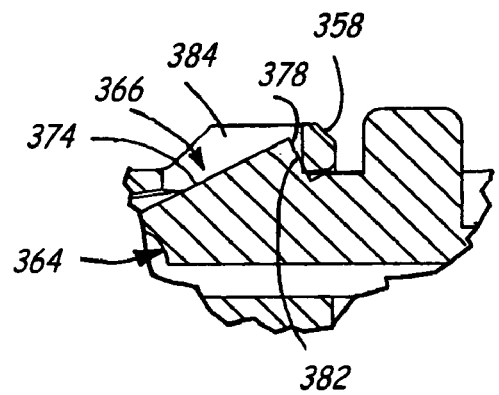
FIG. 14 is a partial sectional view of the alternative embodiment of the present invention of FIGS. 11 and 12.

To lock the arm 352 to the main body 358, the distal portion 354 of the arm 352 is inserted within the receiving portion 358 of the docking member 352. A forward inclined surface 374 of the locking member 364 engages the receiving portion 358, whereby further positioning of the distal portion 354 within the receiving portion 358 causes the receiving portion 358 to urge the locking member 364 deeper within the channeled groove 366 against the bias of the leaf spring 368. Upon traveling past the length of the inclined surface 374, the leaf spring 368 urges the locking member into a slotted aperture 376 positioned within the receiving portion 358, thereby positioning an abutting surface 378 into engagement with a forward inner surface 386 of the slotted aperture 376 to lock the arm 352 to the docking member 356 as illustrated in FIG. 14. Rotational movement of the docking member 356 relative to the arm 352 is prevented by outward side surfaces 382 of the locking member 364 engaging inner surfaces 384 of the slotted aperture 376. Translational movement of the docking member 356 relative arm 352 is also prevented by the locking member 364 engaging the slotted aperture 376 of the receiving portion 358.

To disengage the locking mechanism 362 and remove the arm 352 from the docking member 356 a finger tab 386 connected to the locking member 356 is depressed to disengage the abutting surface 378 from the forward inner surface 380 of the slotted aperture 366. Upon such disengagement, the end portion 354 of the arm 352 is slidably removable from the main body 358.

Figure 15:
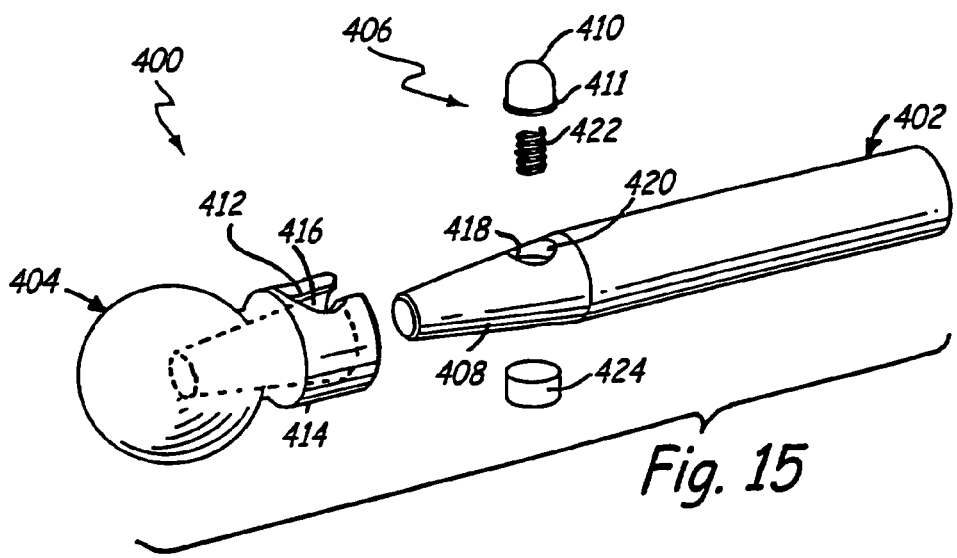
FIG. 15 is an exploded view of another alternative embodiment of the docking assembly of the present invention.
Figure 16:
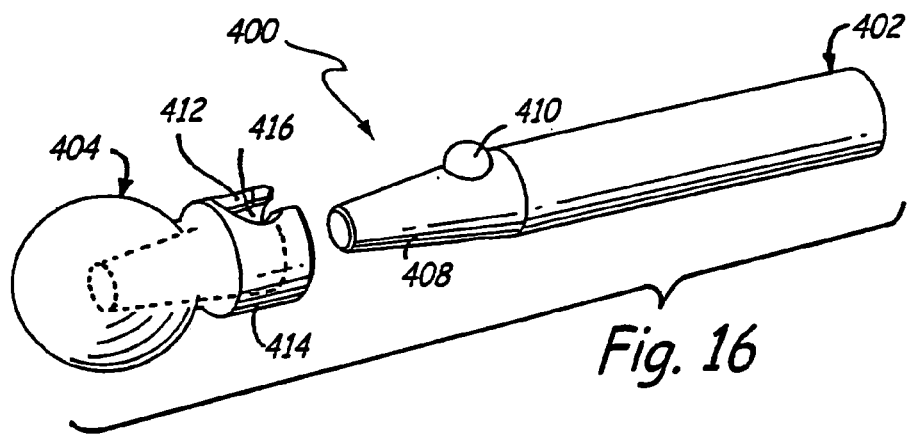
FIG. 16 is another exploded view of the alternative embodiment of the docking assembly of the present invention.
Figure 17:
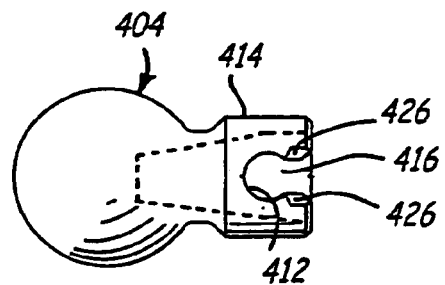
FIG. 17 is a top view of the docking portion of the alternative embodiment illustrated in FIGS. 15 and 16.

Another embodiment of the docking apparatus of the present invention is generally indicated at 400 in FIGS. 15–17. The docking apparatus includes a support arm 402 that engages a ball-type docking member 404 and is retained within a cavity 416 of the main body 414 of the member 404 with a locking mechanism 406.

The support arm 402 includes an end portion 408 having a frusto-conical configuration that is positioned within the cavity 416 that cooperably receives and mates with the end portion 408 of the support arm 402. It should be noted, however, that other configurations of the end portion 408 are within the scope of the present invention, including a cylindrical configuration, a cylindrical configuration having a lesser diameter than the support arm and a conical configuration.

The locking mechanism 406 includes a domed compressible plug 410 positioned within a cylindrical cavity 418 of the end portion 408 of the support arm 402. The plug 410 engages a circular aperture 412 located on the main body 414 of the docking member 404. The plug 410 includes a lower lip 411 to engage inner surfaces 420 within the cylindrical cavity 418 to prevent the plug 410 from escaping from the cylindrical cavity 418. A compressible spring 422 is positioned within the cavity 418 between a 424 and the domed plug 410 where the compressible spring 422 acts upon both the cap 424 and the domed plug 410.

Upon inserting the end portion 408 into the cavity 418 of the main body 414, the plug 410 engages downwardly angled surfaces 426 of the main body 414 proximate to the circular aperture 416. The downwardly angled surfaces 426 engage the domed surface of the plug 410 and force the plug 410 within the cylindrical cavity 418 by overcoming the bias of the compressible spring 422. Upon traveling past the downwardly angled surfaces 426, the compressible spring 422 urges the plug 410 to seat within the circular aperture 416 of the main body 414, thereby securing the support arm 402 to the docking member 404.

To remove the support arm 402 from the internal cavity 416 of the main body 414, the plug 410 is forced into the cavity 418 by overcoming the bias of the compressible spring 422 which displaces the plug 410 from the circular aperture 412. With the plug 410 displaced from the circular aperture 412, the end portion 408 of the support arm 402 is removed from the main body 414.

Figure 18:
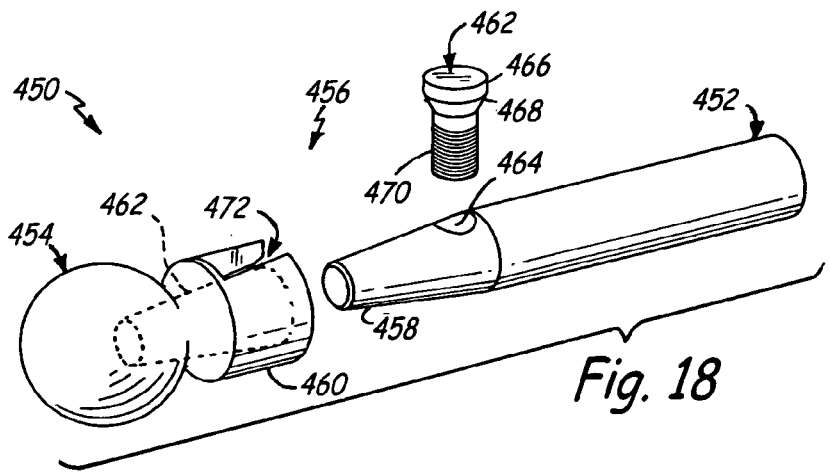
FIG. 18 is an exploded view of another alternative embodiment of the docking assembly of the present invention.
Figure 19:
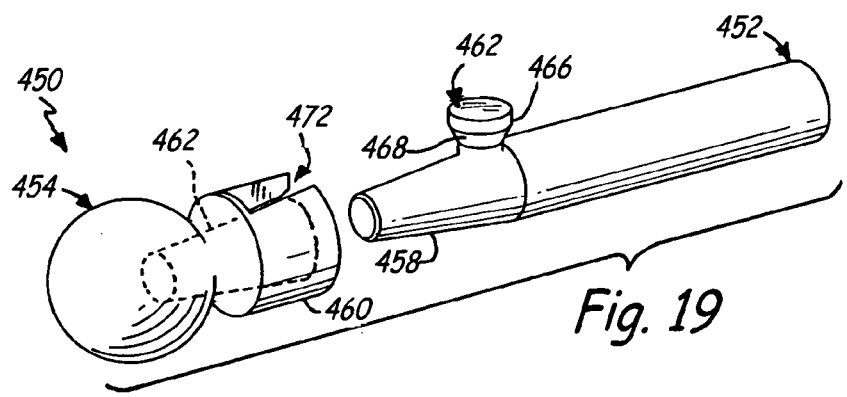
FIG. 19 is another exploded view of the alternative embodiment of the docking assembly of the present invention.
Figure 20:
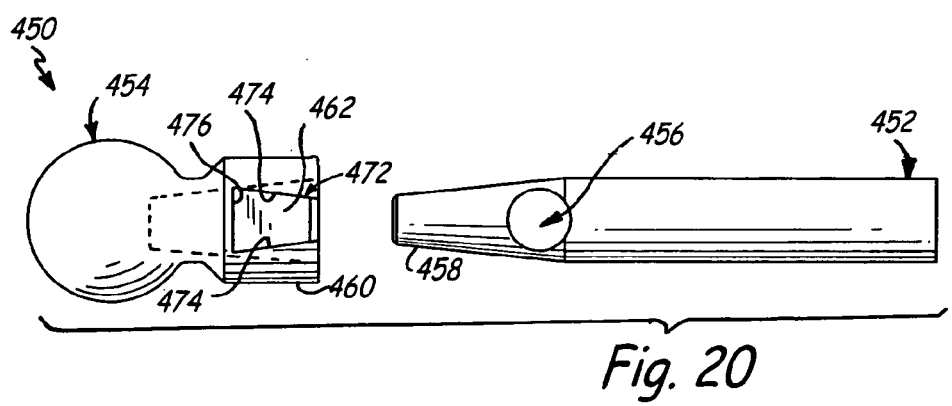
FIG. 20 is a top view of the alternative embodiment of the docking assembly of the present invention as illustrated in FIGS. 18 and 19.
Figure 21:
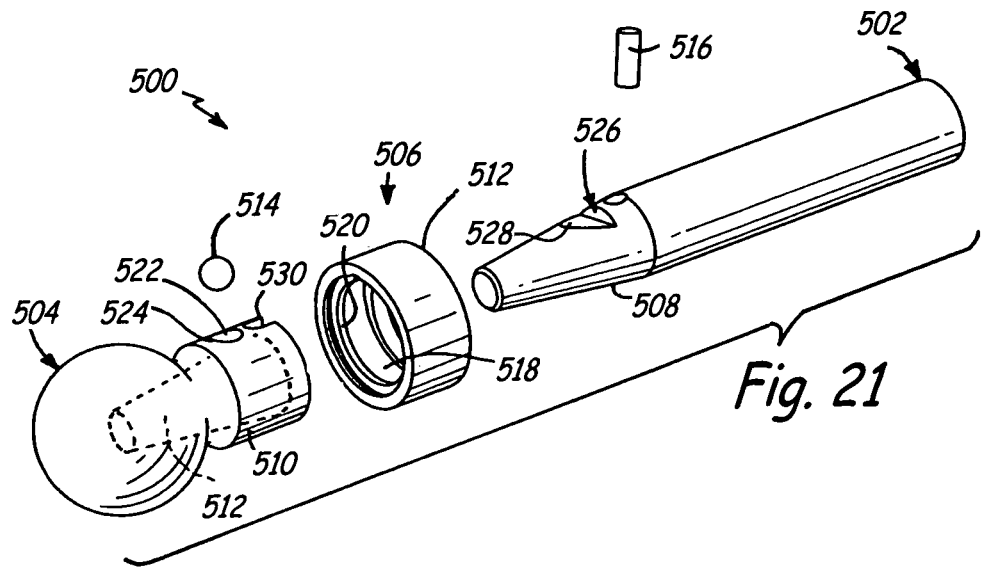
FIG. 21 is an exploded view of another alternative embodiment of the docking assembly of the present invention.
Figure 22:
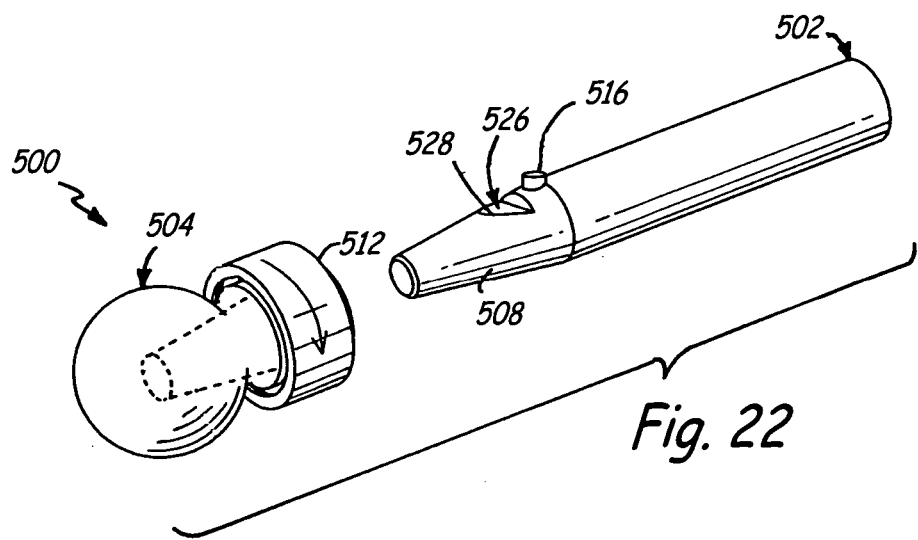
FIG. 22 is another exploded view of the alternative embodiment of the docking assembly of the present invention.

Another embodiment of a docking apparatus of the present invention is generally indicated at 450 in FIGS. 18–20. The docking apparatus 450 includes a support arm 452 securable to a ball-type docking member 454 by a locking mechanism 456. The support arm 452 includes an end portion 458 having a frusto-conical configuration that is positioned within a cavity 462 of a main body 460 of the docking member 454. The cavity 462 cooperably receives and mates with the end portion 458 of the support arm 452. Upon inserting the end portion 458 of the support arm 452 within the cavity 462, the locking mechanism 456 secures the support arm 452 to the docking member 454 and prevents both rotational and translational movement of the support arm 452 relative to the docking member 454.

The locking mechanism 456 includes a fastener 462 threadably engaged within a threaded aperture 464 positioned within the end portion 458. Preferably, the fastener 462 includes an upper portion 466 having a frusto-conical surface 468 and a threaded shaft portion 470 that engages the threaded aperture 464. The locking mechanism 456 further includes a slot 472 positioned within the receiving portion 460. The slot 472 includes side surfaces 474 spaced apart an initial distance to receive only the shaft portion 470 of the fastener 462. The distance between each side surface 474 gradually increases to a rear surface 476 of the slot 472. Each side surface 474 is also beveled to cooperably engage the frusto-conical surface 468 of the fastener 462.

The support arm 452 is secured to the main body 460 by positioning the end 458 within the cavity 462 of the docking member 454. The fastener 462 is positioned within the end portion 458 where the frusto-conical surface 468 of the end portion 466 frictionally engages the beveled side surfaces 474 of the slot 472. The frictional engagement of the side surfaces 474 of the slot 472 with the frusto-conical portion 468 of the fastener 462 prevents both rotational and translational movement of the support arm 452 relative to the docking member 454.

To remove the support arm 452 from the docking member 454, the frusto-conical surface 468 of the locking mechanism 456 is disengaged from the beveled side surfaces 474 by either completely removing or partially removing the threaded fastener 462. Partially removing or completely removing the threaded fastener 462 allows the shaft portion 470 to travel between the side surfaces 474 of the slotted aperture 472 such that the support arm 452 is removed from the docking member 454.

Another embodiment of a docking apparatus of the present invention is generally indicated at 500 in FIGS. 21–24. The embodiment 500 of the present invention includes a support arm 502 securable to a ball-type docking member 504 by means of a locking mechanism 506. The support arm 502 includes an end portion 508 having a frusto-conical configuration that is positioned within an internal cavity 572 of a main body 510 of the docking member 504.

With the end portion 508 positioned within the cavity 512 of the main body 510, the locking mechanism 506 secures the support arm 502 to the docking member 504. The locking mechanism 506 includes a collet 512 that engages a ball 514 positioned within the main body 510 and a peg 516 positioned within the end portion 508 to secure the end portion 508 to the docking member 504.

Figure 23:
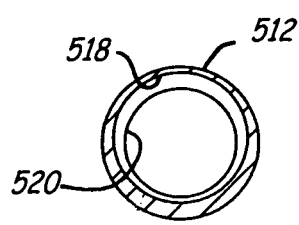
FIG. 23 is a sectional view of the collet of the alternative embodiment of the docking assembly illustrated in FIGS. 21 and 22.
Figure 24:
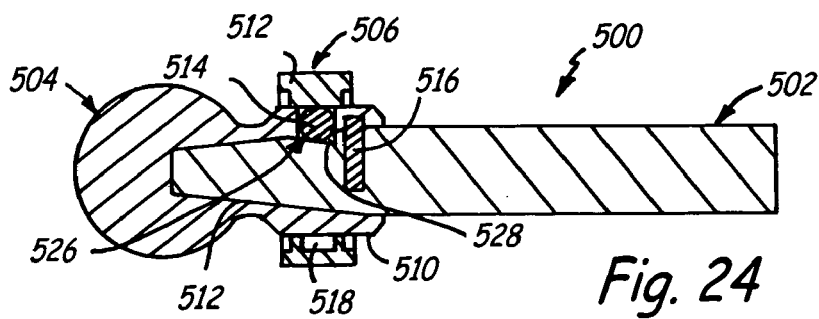
FIG. 24 is a sectional view of the alternative embodiment of the present invention illustrated in FIGS. 21 and 22.
Figure 29:
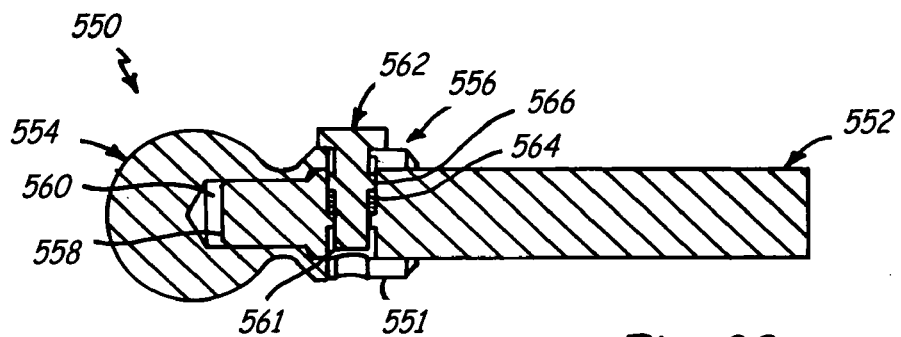
FIG. 29 is another sectional view of the alternative embodiment of the docking assembly of the present invention as illustrated in FIGS. 25 and 26.

As illustrated in FIG. 23, the collet 512 includes an inner eccentric surface 518 having a spiraled groove 520 for engaging the ball 514. The ball 514 is positioned within a spherical cavity 522 on the main body 510. The cavity 522 is formed to accept the ball 514 from an outer surface 524 of the receiving portion 510, but the inner surface (not shown) contains an aperture having a diameter slightly less than the diameter of the ball 514 which limits the travel of the ball 514.

The collet 512 is positioned over the main body 510 such that the ball 514 seats within the groove 520. The ball 514 engages a notched area 526 having a beveled surface 528 on the end portion 508 of the support arm 502. Upon inserting the end portion 508 into the cavity 512 of the main member 510, the peg 516 engages a slot 530 on the main body 510 to prevent rotational movement of the support arm 502 relative to the docking member 504. The collet 512 is rotated and the inner eccentric surface 518 urges the ball 514 towards the notched area 526 of the end portion 508. The ball 514 is forced into the notched area 526 and engages both the beveled surface 528 of the end portion 508 and the inner surface 518 of the collet 512 to retain the support arm 502 within the docking member 504.

To disengage the support arm 502 from the docking member 504, the collet 512 is rotated in the opposite direction such that the inner eccentric surface 518 allows the beveled surface 528 of the notched area 526 to urge the ball 514 within the cavity 522. With the ball 514 within the cavity 522, the support arm 502 is removable from the docking member 504.

Another embodiment of the docking assembly of the present invention is generally indicated at 550 in FIGS. 25–29. The docking assembly 550 includes a support arm 552 that is secured to a ball-type docking member 554 by a locking mechanism 556. The support arm 552 includes an end portion 558 having a cylindrical configuration with a diameter less than the support arm 552 where the end portion 538 is positioned within a cavity 560 of a main body 557 of the docking member 554. With the end portion 558 positioned within the cavity 560, the locking mechanism 556 secures the support arm 552 to the docking member 554.

Figure 27:
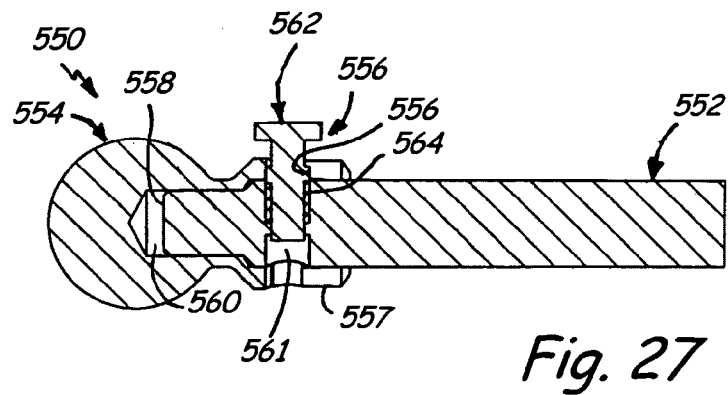
FIG. 27 is a sectional view of the alternative embodiment of the docking assembly of the present invention as illustrated in FIGS. 25 and 26.

The locking mechanism 556 includes a plunger 562 that is partially positioned within the support arm 552. The plunger 562 is positionable between a first extended position as illustrated in FIG. 27 and a second plunged position as illustrated in FIG. 28. A compressible spring 564 positioned within a recess 561 in the support arm 552 biases the plunger 562 towards the first extended position. The plunger 562 further includes a circular band 566 that is exposed when the plunger 562 is in the first extended position and where the band 566 is positioned within the recess 561 when the plunger 562 is in the plunged position.

The receiving portion 557 further includes a slotted aperture 568 and a circular aperture 570 positioned to cooperably act in conjunction with one another. The slotted aperture 568 has a width that coincides with the diameter of the plunger 562, while the circular aperture 570 has a diameter which coincides with an outer diameter of the circular band 566.

Upon inserting the end portion 558 of the support arm 552 within the cavity 560 of the main body 557 of the docking member 554, the plunger 562 is urged with manual force into the plunged position by overcoming the bias of the spring 564 which positions the circular band 566 within the recess 561 of the support arm 552. The plunger 562 travels through the slotted aperture 568 toward the circular aperture 570. With the plunger 562 positioned proximate the circular aperture 570, the spring 564 urges the plunger 562 towards the extended position, thereby positioning the circular band 566 within the circular aperture 570 and locking the support arm 552 to the docking member 554.

With the circular band 566 positioned within the circular aperture 570 of the receiving member 557 the support arm 552 is secured to the docking member 554. To disengage the docking member 554 from the support arm 552, the plunger 562 is manually forced into the plunged position where the band 566 is positioned within the recess 561 such that the plunger 562 travels along the slotted aperture 568 as the support art 552 is removed from the docking member 554.

Figure 32:
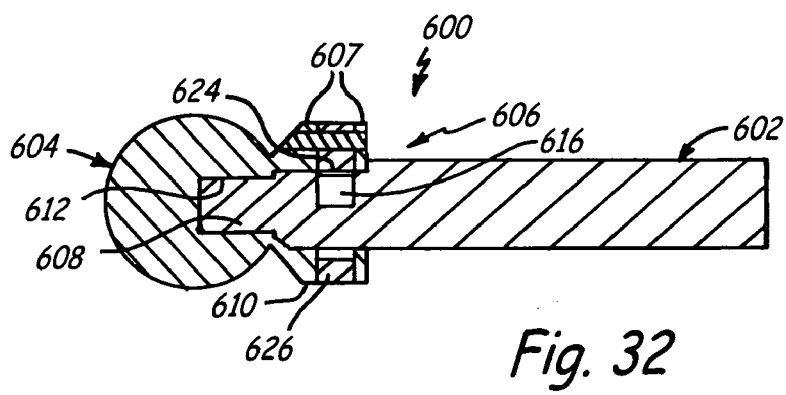
FIG. 32 is a sectional view of the alternative embodiment of the docking assembly of the present invention illustrated in FIGS. 30 and 31.
Figure 25:
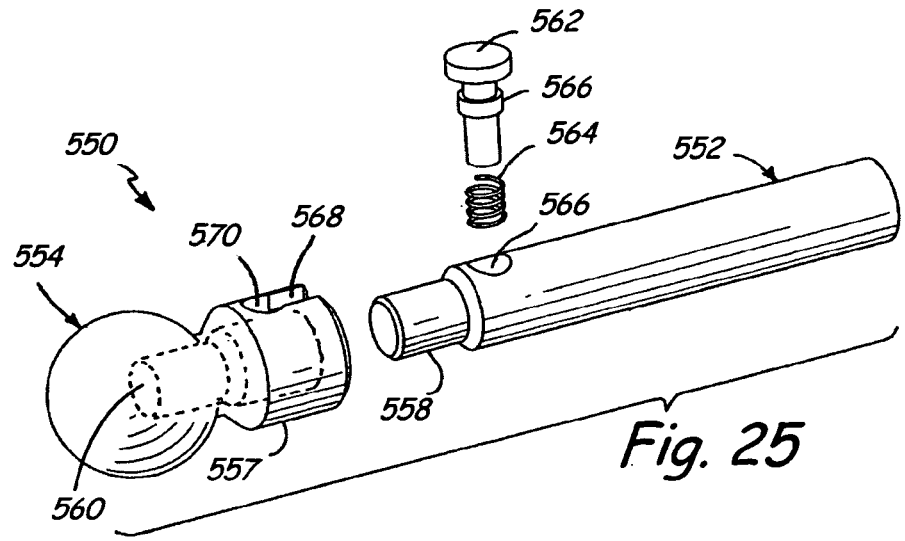
FIG. 25 is an exploded view of another alternative embodiment of the docking assembly of the present invention.
Figure 26:
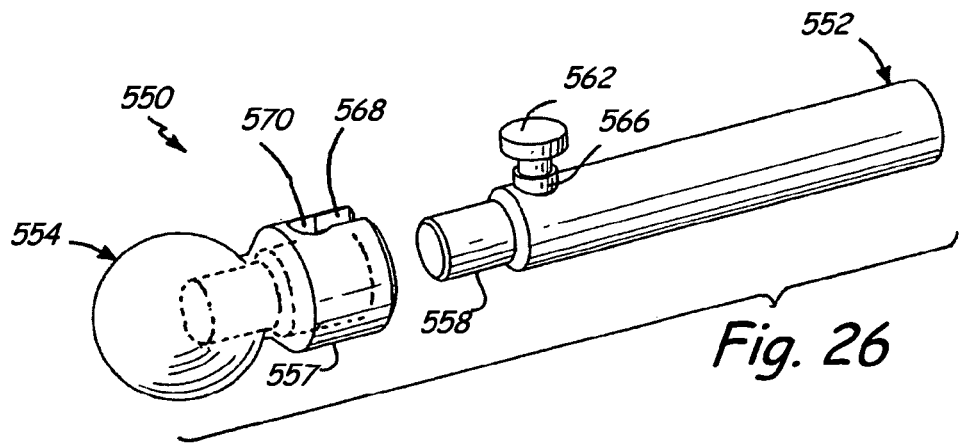
FIG. 26 is an additional exploded view of the alternative embodiment of the docking assembly of the present invention
Figure 30:
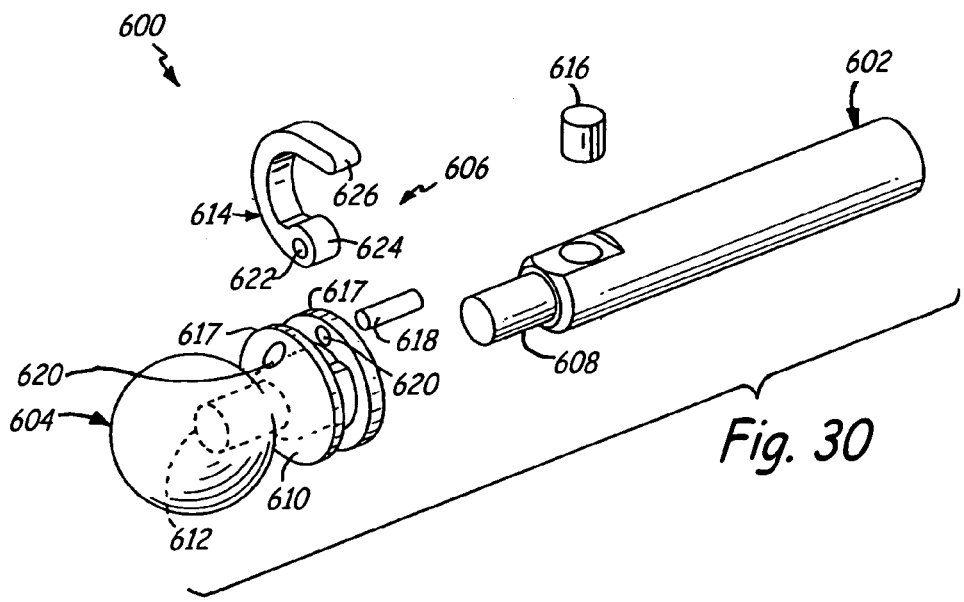
FIG. 30 is an exploded view of another alternative embodiment of the docking assembly of the present invention.
Figure 31:
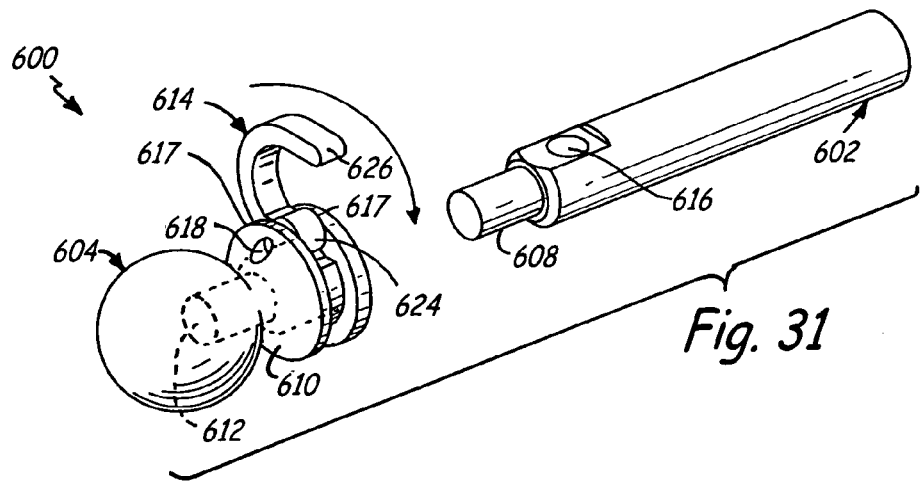
FIG. 31 is an additional exploded view of the alternative embodiment of the docking assembly of the present invention.

Another embodiment of the docking assembly of the present invention is generally depicted at 600 in FIGS. 30–32. The docking assembly 600 generally includes a support arm 602 securable to a ball-type docking member 604 with a locking mechanism 606. The support arm 602 includes an end portion 608 having a cylindrical configuration, preferably with a lesser diameter than the support arm 602 that is positioned within a cavity 612 in a main body 610 of the docking member 604. The cavity 612 also receives a portion of the support arm 602. With the end portion 608 positioned in the cavity 612 of the main body 610, the locking mechanism 606 secures the support arm 602 to the docking member 604.

The locking mechanism 606 includes a clasp 614 pivotally attached to the receiving portion 610 that engages a compressible member 616 positioned within the support arm 602. The clasp 614 is secured between inner and outer flanges 617 and pivotally attached to a pin 618. The pin 618 is positioned within apertures 620 in each flange 617 and an aperture 622 within the clasp 614.

The locking clasp 614 is positionable between a non-engaging position, as illustrated in FIG. 31, and an engaged position, as illustrated in FIG. 32, wherein the locking mechanism 606 secures the support arm 602 to the docking member 604. With the locking clasp 614 in the non-engaging position, the end portion 608 of the support arm 602 is inserted within the cavity 612 of the main body 610 of the docking member 604. Positioning the locking clasp 614 towards the engaged position causes a cammed surface 624 to engage and slightly compress the compressible member 617, thereby frictionally engaging and securing the support arm 602 to the docking member 604. Further pivoting the locking clasp 614 engages a distal portion 626 of the clasp 614 with the main body 610 to frictionally lock the clasp 614 in the engaged position.

To remove the support arm 602 from the docking member 604, the locking clasp 614 is positioned toward the non-engaged position, which disengages the cammed surface 624 from the compressible member 617. Manual force is applied to the support arm 602 to remove the end portion 608 of the support arm 602 from the main body 610.

Figure 33:
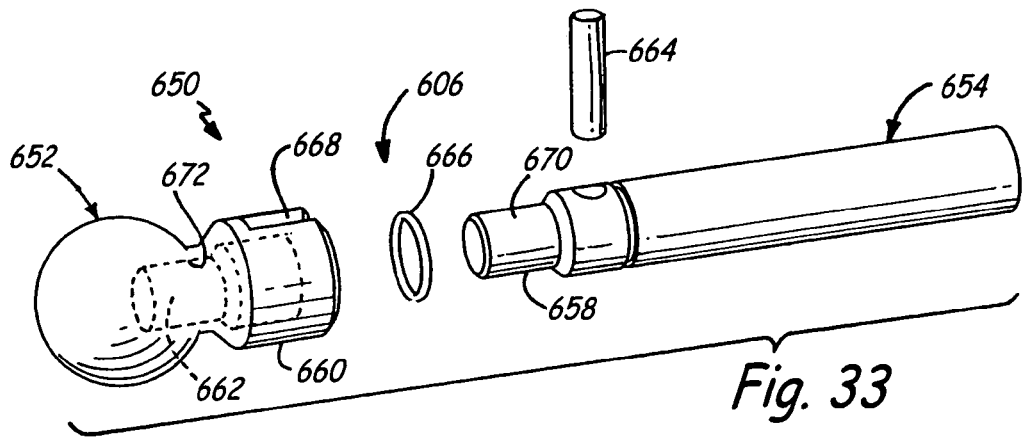
FIG. 33 is an exploded view of another alternative embodiment of the docking assembly of the present invention.
Figure 34:
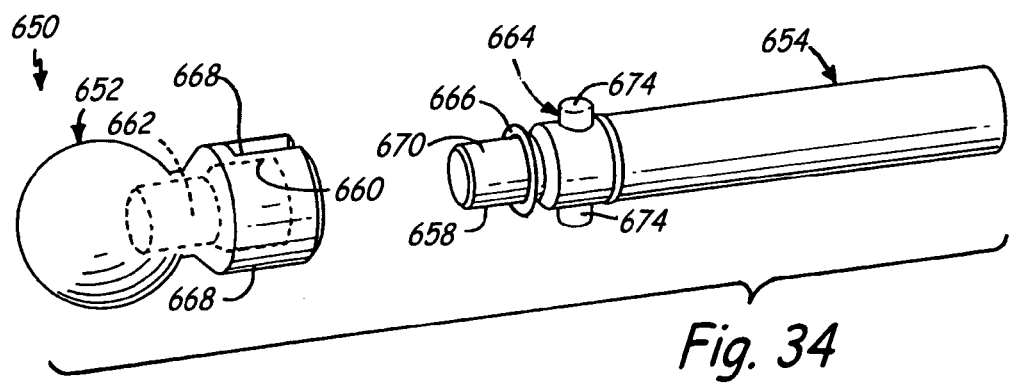
FIG. 34 is another exploded view of the alternative embodiment of the docking assembly of the present invention.
Figure 35:
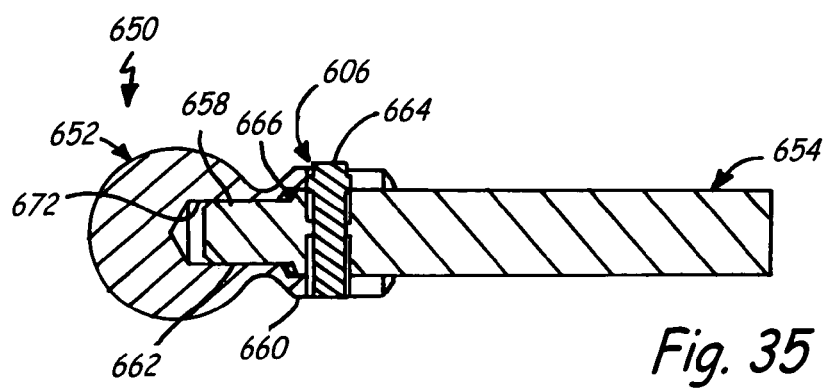
FIG. 35 is a sectional view of the alternative embodiment of the docking assembly of the present invention illustrated in FIGS. 33 and 34.

Another embodiment of the docking assembly of the present invention is generally indicated at 650 in FIGS. 33–35. The docking assembly 650 includes a support arm 654 that is secured to a docking member 652 with a locking mechanism 656. The support arm 654 includes an end portion 658 having a cylindrical configuration, where the end portion 658 is inserted into a cavity 662 of the main body 660 of the docking member 652.

The locking mechanism includes a peg 664 disposed within the support arm 652, a pliable ring 666 disposable about the end portion 658 of the support arm 652, and slotted apertures 668 longitudinally positioned within the main body 660 to receive the peg 664. With the end portion 658 of the support arm 654 positioned within the cavity 662 of the main body 660 of the docking member 652, the pliable ring 666 engages an outer surface 670 of the end portion 658 and an inner surface 672 of the cavity 662 of the main body 660 to frictionally secure the support arm 654 within the docking member 652.

The main body 660 also partially receives the support arm 654. Further positioning of the end portion 658 into the cavity 662 forces ends 674 of the peg 664 to be positioned within each respective slotted aperture 668 to prevent rotational movement of the support arm 654 relative to the docking member 604. As the locking clasp 614 pivots, a distal portion 626 of the clasp 614 engages the main body 610 to frictionally lock the clasp 614 in the engaged position.

To remove the support arm 654 from the docking member 652, manual force is applied to the support arm 654 in a direction away from the docking member 652, to overcome the frictional engagement of the pliable ring 666 between the end portion 658 and the main body 660. Upon overcoming the frictional engagement, the support arm 654 is removable from cavity 662 of the main body 660.

Figure 36:
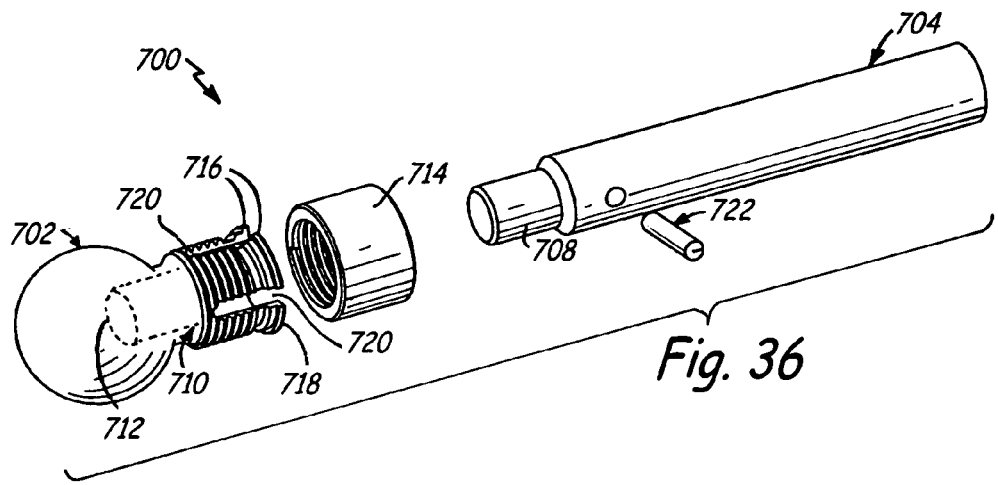
FIG. 36 is an exploded view of another alternative embodiment of the docking assembly of the present invention.
Figure 37:
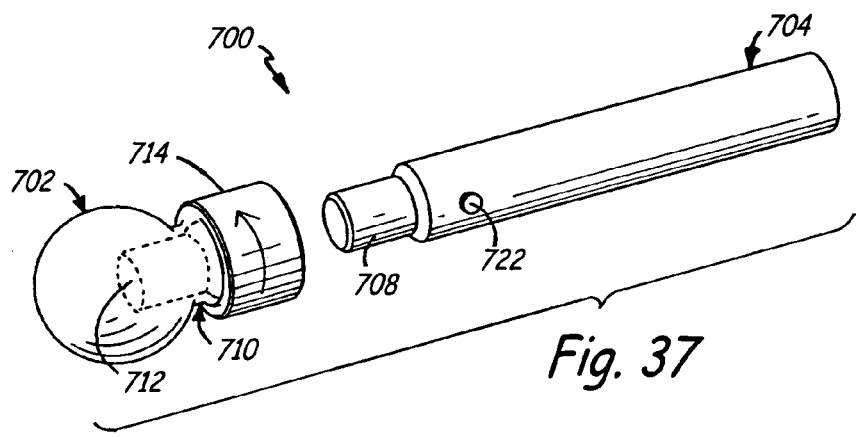
FIG. 37 is another exploded view of the alternative embodiment of the docking assembly of the present invention.
Figure 38:
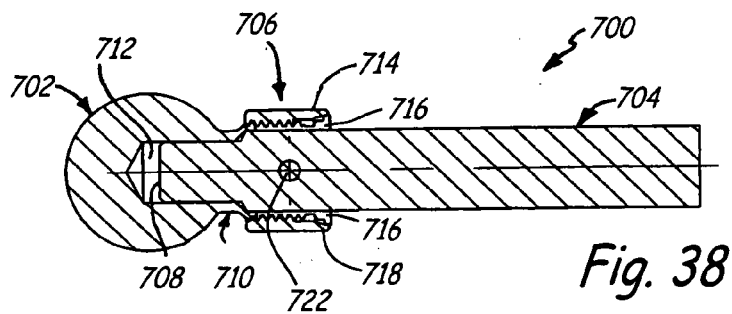
FIG. 38 is a sectional view of the alternative embodiment of the docking assembly of the present invention illustrated in FIGS. 36 and 37.

Another embodiment of the docking assembly of the present invention is generally indicated at 700 in FIGS. 36–38. The docking assembly 700 includes a support arm 704 that is secured to a ball type docking member 702 with a locking mechanism 706. The support arm 704 includes an end portion 708 having a cylindrical configuration, preferably having a lesser diameter than a diameter of the support arm 704, that is positioned within an inner cavity 712 of the main body 710 of the docking member 702.

The locking mechanism 706 includes a threaded collet 714 that engages the main body 710 to compress a plurality of legs 716 into frictional engagement with the support arm 704. Each leg 716 includes a threaded outer surface 718 that threadably engage the threaded collet 714. Each leg 716 is also positioned relative to one another to form a plurality of slots 720.

After positioning the end portion 708 of the support arm 704 into the cavity 712 of receiving portion 710 of the docking member 702, a peg 722 disposed within the support arm 704 is disposed within the respective slots 720 to prevent rotational movement of the support arm 704 relative to the docking member 702. With the end portion 708 of the support arm 704 within the cavity 712 of the receiving portion 710, the collet 714 is rotated to force each leg 716 into frictional engagement with the support arm 704, thereby securing the support arm 704 to the docking member 702.

To remove the support arm 704 from the docking member 702, the collet 714 is rotated in the opposite direction resulting in each leg 716 flexing away from the end portion 708. Manual force is applied to the support arm 704 to remove the end portion 708 from the cavity 712 of the main body 710.

Although the present invention has been described with reference to preferred embodiments, workers skilled in the art will recognize that changes may be made in form and detail without departing from the spirit and scope of the invention.

What is claimed is:

1. An assembly for exchanging retractor support arms within a retractor support clamp, the assembly comprising:
   a main body having a surface defining a cavity extending into the main body from a first end and at least one through bore intersecting the cavity;
   a pivot ball attached to a second end of the main body wherein the pivot ball engages the retractor support clamp;
   a support arm having an end portion having a substantially complimentary configuration to the surface defining the cavity wherein the end portion is positionable within the cavity; and
   a retaining mechanism disposed about the main body and in communication with the end portion for retaining the end portion within the main body; and
   wherein the retaining mechanism comprises:
      at least one spheroidal member positioned within the through bore wherein the spheroidal member has a first portion extending into the cavity and a second portion extending beyond an outer surface of the main body; and
      a housing having a through bore wherein the housing is disposed about the main body and moveable thereon wherein an engaging surface which defines a portion of the through bore engages the second portion of the spheroidal member and forces the first portion of the spheroidal member into the end portion when the housing retains the end portion within the main body.

2. The assembly of claim 1 wherein the engaging surface has a frusto-conical configuration.

3. The assembly of claim 1 wherein the end portion further comprises an annular groove and wherein the first portion of the spheroidal member is disposed within the annular groove and retains the end portion within the main body when the housing is in the first position.

4. The assembly of claim 1 wherein the cavity has a substantially non-round first surface.

5. The assembly of claim 4 wherein the end portion of the retractor support arm has a substantially non-round second surface wherein the second surface engages the first surface to prevent rotation of the end portion of the support arm within the cavity.

6. The assembly of claim 1 and further comprising a compression spring disposed about the main member and in communication with the retaining mechanism wherein the compression spring biases the retaining mechanism into retaining the end portion.

7. A docking apparatus for exchanging retractor support arms within a retractor support apparatus, the docking apparatus comprising:
- a main body attached to the retractor support apparatus, the main body comprising an internal cavity;
- a support arm having an end comprising a substantially complementary configuration to the internal cavity within the main body wherein the end is positionable within the internal cavity; and
- a securing mechanism engaging the end of the support arm and the main body wherein the securing mechanism applies a force to the end of the support arm and the main body to retain the end of the support arm within the main body and wherein the end has an axis offset from an axis of the support arm such that when the end is positioned within the cavity the offset axis of the end prevents rotational movement of the end within the cavity.

8. The apparatus of claim 7 wherein the securing mechanism comprises a coiled flexible spring positioned within the internal cavity and wherein when the end is positioned within the internal cavity the coil flexible spring retains the end within the cavity of the main.

9. The apparatus of claim 7 wherein the end comprises a non-round portion that engages a non-round port of the internal cavity to prevent rotation of the end within the cavity.

10. An assembly for exchanging retractor support arms within a retractor support clamp, the assembly comprising:
- a main body having, a surface defining a cavity extending into the main body from a first end;
- a support arm having an end portion having a substantially complimentary configuration to the surface defining the cavity wherein the end portion is positionable within the cavity; and
- a retaining mechanism disposed about the main body and in communication with the end portion for retaining the end portion within the main body wherein the retaining mechanism comprises:
- at least one spheroidal member positioned within a through bore wherein the spheroidal member has a first portion extending into the cavity and a second portion extending beyond an outer surface of the main body; and
- a housing having a through bore wherein the housing is disposed about the main body and moveable thereon wherein an engaging surface which defines a portion of the through bore engages the second portion of the spheroidal member and forces the first portion of the spheroidal member into the end portion when the housing retains the end portion within the main body.

11. The assembly of claim 10 wherein the engaging surface has a frusto-conical configuration.

12. The assembly of claim 10 wherein the end portion further comprises an annular groove and wherein the first portion of the spheroidal member is disposed within the annular groove and retains the end portion within the main body when the housing is in the first position.

* * * * *